US 9,101,782 B2

(12) United States Patent
Frustaci et al.

(10) Patent No.: US 9,101,782 B2
(45) Date of Patent: Aug. 11, 2015

(54) IMPLANTABLE CARDIOVERTER DEFIBRILLATOR DESIGNED FOR USE IN A MAGNETIC RESONANCE IMAGING ENVIRONMENT

(71) Applicant: Greatbatch Ltd., Clarence, NY (US)

(72) Inventors: Dominick J. Frustaci, Williamsville, NY (US); Barry C. Muffoletto, Alden, NY (US); Robert A. Stevenson, Canyon Country, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/958,582

(22) Filed: Aug. 4, 2013

(65) Prior Publication Data

US 2013/0317345 A1    Nov. 28, 2013

Related U.S. Application Data

(62) Division of application No. 13/589,090, filed on Aug. 18, 2012, now abandoned.

(60) Provisional application No. 61/525,235, filed on Aug. 19, 2011.

(51) Int. Cl.
*A61N 1/39* (2006.01)
*A61N 1/37* (2006.01)
*A61B 5/055* (2006.01)

(52) U.S. Cl.
CPC ............ *A61N 1/3987* (2013.01); *A61B 5/0555* (2013.01); *A61N 1/3718* (2013.01); *A61N 1/3925* (2013.01); *A61N 1/3962* (2013.01)

(58) Field of Classification Search
CPC . A61N 1/3718; A61N 1/3754; A61N 1/3962; A61N 1/3987; A61B 5/0555
USPC ............... 607/31–32, 9, 34, 62–63, 115–116, 607/119; 600/410–411
See application file for complete search history.

(56) References Cited

U.S. PATENT DOCUMENTS

| 3,681,612 A | 8/1972 | Vogl et al. |
| 3,745,430 A | 7/1973 | Lunquist et al. |
| 4,424,551 A | 1/1984 | Stevenson et al. |

(Continued)

FOREIGN PATENT DOCUMENTS

| JP | 6176962 | 6/1994 |
| JP | 7272975 | 10/1995 |

(Continued)

*Primary Examiner* — Catherine Voorhees
(74) *Attorney, Agent, or Firm* — Marc G. Martino

(57) ABSTRACT

An implantable cardioverter defibrillator includes a communication interface operable to receive a communication signal from an external programmer. The communication signal includes a command to switch the ICD from a first mode to a second mode. A processor is in electrical communication with the communication interface and configured to switch the ICD between the first and second modes. A battery is configured to supply low DC voltage. A converter is configured to convert the low DC voltage to a high DC voltage. An energy storage capacitor is electrically coupled to the converter and configured to store a therapeutic energy or high DC voltage including at least 15 joules. The second mode includes activating the converter to convert the low DC voltage to the high DC voltage and storing the therapeutic energy or at least 15 joules within the energy storage capacitor during a period of time of the second mode.

21 Claims, 15 Drawing Sheets

(56) References Cited

U.S. PATENT DOCUMENTS

| | | |
|---|---|---|
| 4,858,064 A | 8/1989 | Segawa et al. |
| 5,039,965 A | 8/1991 | Higgins, Jr. |
| 5,268,810 A | 12/1993 | DiMarco et al. |
| 5,331,505 A | 7/1994 | Wilheim |
| 5,333,095 A | 7/1994 | Stevenson et al. |
| 5,450,090 A | 9/1995 | Gels et al. |
| 5,491,300 A | 2/1996 | Huppenthal et al. |
| 5,493,259 A | 2/1996 | Blalock et al. |
| 5,620,476 A | 4/1997 | Truex et al. |
| 5,650,759 A | 7/1997 | Hittman et al. |
| 5,683,435 A | 11/1997 | Truex et al. |
| 5,757,252 A | 5/1998 | Cho et al. |
| 5,765,779 A | 6/1998 | Hancock et al. |
| 5,782,891 A | 7/1998 | Hassler et al. |
| 5,822,174 A | 10/1998 | Yamate et al. |
| 5,905,627 A | 5/1999 | Brendel et al. |
| 5,929,729 A | 7/1999 | Swarup |
| 5,959,336 A | 9/1999 | Barsan |
| 5,973,906 A | 10/1999 | Stevenson et al. |
| 5,973,907 A | 10/1999 | Reed |
| 6,137,161 A | 10/2000 | Gilliland et al. |
| 6,146,743 A | 11/2000 | Haq et al. |
| 6,373,673 B1 | 4/2002 | Anthony |
| 6,424,234 B1 | 7/2002 | Stevenson |
| 6,456,481 B1 | 9/2002 | Stevenson |
| 6,459,935 B1 | 10/2002 | Piersma |
| 6,473,314 B1 | 10/2002 | Custer et al. |
| 6,512,666 B1 | 1/2003 | Duva |
| 6,529,103 B1 | 3/2003 | Brendel et al. |
| 6,566,978 B2 | 5/2003 | Stvenson et al. |
| 6,660,116 B2 | 12/2003 | Wolf et al. |
| 6,765,780 B2 | 7/2004 | Brendel et al. |
| 6,768,630 B2 | 7/2004 | Togashi |
| 6,806,806 B2 | 10/2004 | Anthony |
| 7,038,900 B2 | 5/2006 | Stevenson et al. |
| 7,110,227 B2 | 9/2006 | Anthony et al. |
| 7,113,387 B2 | 9/2006 | Stevenson et al. |
| 7,199,995 B2 | 4/2007 | Stevenson |
| 7,236,834 B2 | 6/2007 | Christopherson et al. |
| 7,301,748 B2 | 11/2007 | Anthony et al. |
| 7,310,216 B2 | 12/2007 | Stevenson et al. |
| 7,322,832 B2 | 1/2008 | Kronich et al. |
| 7,327,553 B2 | 2/2008 | Brendel |
| 7,363,090 B2 | 4/2008 | Halperin |
| 7,423,860 B2 | 9/2008 | Anthony et al. |
| 7,428,136 B2 | 9/2008 | Barnett |
| 7,433,168 B2 | 10/2008 | Anthony |
| 7,436,672 B2 | 10/2008 | Ushijima et al. |
| 7,439,449 B1 | 10/2008 | Kumar et al. |
| 7,446,996 B2 | 11/2008 | Togashi |
| 7,450,396 B2 | 11/2008 | Ye et al. |
| 7,495,884 B2 | 2/2009 | Togashi |
| 7,586,728 B2 | 9/2009 | Anthony |
| 7,593,208 B2 | 9/2009 | Anthony et al. |
| 7,675,729 B2 | 3/2010 | Anthony et al. |
| 7,679,926 B2 | 3/2010 | Hsu et al. |
| 7,702,387 B2 | 4/2010 | Stevenson et al. |
| 7,719,854 B2 | 5/2010 | Youker et al. |
| 7,733,621 B2 | 6/2010 | Anthony et al. |
| 2004/0220626 A1 * | 11/2004 | Wagner .............................. 607/4 |
| 2005/0201039 A1 | 9/2005 | Stevenson et al. |
| 2006/0032665 A1 | 2/2006 | Ice |
| 2006/0085043 A1 | 4/2006 | Stevenson |
| 2006/0212096 A1 | 9/2006 | Stevenson |
| 2007/0112398 A1 | 5/2007 | Stevenson |
| 2007/0123949 A1 | 5/2007 | Dabney et al. |
| 2007/0203529 A1 | 8/2007 | Iyer et al. |
| 2007/0288058 A1 | 12/2007 | Halperin et al. |
| 2008/0049376 A1 | 2/2008 | Stevenson |
| 2008/0049410 A1 | 2/2008 | Kawaguchi et al. |
| 2008/0071313 A1 | 3/2008 | Stevenson |
| 2008/0116997 A1 | 5/2008 | Dabney |
| 2008/0132987 A1 | 6/2008 | Westlund |
| 2008/0158746 A1 | 7/2008 | Anthony et al. |
| 2008/0161886 A1 | 7/2008 | Stevenson |
| 2008/0195180 A1 | 8/2008 | Stevenson et al. |
| 2008/0239622 A1 | 10/2008 | Hsu et al. |
| 2008/0247111 A1 | 10/2008 | Anthony et al. |
| 2008/0247116 A1 | 10/2008 | Kawano et al. |
| 2008/0247117 A1 | 10/2008 | Elam et al. |
| 2008/0264685 A1 | 10/2008 | Park et al. |
| 2008/0277153 A1 | 11/2008 | Teshome et al. |
| 2009/0097219 A1 | 4/2009 | Cho et al. |
| 2009/0107717 A1 | 4/2009 | Hsu et al. |
| 2009/0128976 A1 | 5/2009 | Anthony |
| 2009/0139760 A1 | 6/2009 | Tanaka |
| 2009/0180237 A1 | 7/2009 | Hou et al. |
| 2009/0187229 A1 | 7/2009 | Lavie |
| 2009/0236141 A1 | 9/2009 | Kim et al. |
| 2010/0046135 A1 | 2/2010 | Niki et al. |
| 2010/0046137 A1 | 2/2010 | Adachi |
| 2010/0109958 A1 | 5/2010 | Haubrich et al. |
| 2010/0109966 A1 | 5/2010 | Mateychuk et al. |
| 2010/0149042 A1 | 6/2010 | Utsi et al. |
| 2010/0151113 A1 | 6/2010 | Shelton |
| 2010/0211123 A1 * | 8/2010 | Stubbs et al. .................... 607/4 |
| 2010/0222856 A1 * | 9/2010 | Halperin et al. ............. 607/116 |
| 2011/0137359 A1 * | 6/2011 | Stubbs et al. .................... 607/4 |
| 2011/0160803 A1 * | 6/2011 | Stessman et al. ............... 607/62 |
| 2013/0197596 A1 * | 8/2013 | Cabelka et al. .................. 607/6 |

FOREIGN PATENT DOCUMENTS

| | | |
|---|---|---|
| JP | 2001068958 | 3/2001 |
| JP | 2004254257 | 9/2004 |
| JP | 2004289760 | 10/2004 |
| JP | 2005117606 | 4/2005 |
| JP | 2007129565 | 11/2005 |

* cited by examiner

IMPLANTABLE CARDIOVERTER DEFIBRILLATOR DESIGNED FOR USE IN A MAGNETIC RESONANCE IMAGING ENVIRONMENT

CROSS-REFERENCE TO RELATED APPLICATIONS

This utility application is a divisional application of application Ser. No. 13/589,090 filed Aug. 18, 2012, which itself claimed priority to provisional application 61/525,235 filed on Aug. 19, 2011, the contents of all of which are fully incorporated herein with this reference.

DESCRIPTION

1. Field of the Invention

The present invention generally relates to implantable cardioverter defibrillators. More particularly, the present invention relates to an implantable cardioverter defibrillator that can operate during medical diagnostic procedures such as magnetic resonant imaging.

2. Background of the Invention

Magnetic resonance imaging (MRI) is an efficient technique used in the diagnosis of many disorders, including neurological and cardiac abnormalities and other diseases. MRI has achieved prominence in both the research and clinical arenas. It provides a non-invasive method for examining internal body structures and functions. Because MRI has become such a useful diagnostic tool, it now is used extensively in hospitals and clinics around the world.

Magnetic resonance imaging equipment produces three main electromagnetic fields during operation. In particular, MRI systems generally produce and utilize: 1) the strong static magnetic field also known as $B_0$ (for example, a common 1.5 Tesla MRI scanner has over 100,000 times the strength of the earth's magnetic field); 2) a time-varying gradient field, Gx, Gy and Gz; and 3) a pulsed radio frequency (RF) field (known as B1). The static field produced by most MRI systems has a magnetic induction ranging from about 0.5 to about 3.0 T. The frequency of the RF field used for imaging is related to the magnitude of the static magnetic field, and, for current-generation MRI systems, the frequency of the RF field ranges from about 6.4 to about 128 MHz. The most common MRI system deployed and used today is 1.5 T with an RF-pulsed frequency of 64 MHz. The time-varying gradient field is used in MRI for spatial encoding, and typically has a frequency in the Kilohertz range.

These strong electromagnetic fields produced by MRI systems can cause problems for implantable medical devices and as a result, both the U.S. Food and Drug Administration (FDA) and many pacemaker manufacturers have issued warnings against pacemaker recipients undergoing MRIs. More specifically, it has been documented that implantable cardioverter defibrillators (ICDs) can exhibit a number of malfunctions when placed inside of a clinical MRI scanner bore. First of all, ICDs incorporate a high voltage power supply. This high voltage power supply converts the relatively low DC voltage from the ICD's internal battery to a high voltage DC that is required to charge up the ICD's high energy storage capacitor(s). Once the high energy storage capacitors of the ICD are charged up, they can then deliver a therapeutic shock (typically in the area of 32 to 40 joules). The internal ICD power supply (switch mode or other) does embody ferrite materials, such as a ferrite or iron core transformer. In the presence of the main static $B_0$ field of the MR scanner, these ferrite or iron materials saturate and become very inefficient. It has been documented, that the charging transformer of an ICD will saturate during an MRI scan thereby making it impossible to charge up the ICD's high energy storage capacitor to a high enough voltage level.

It has also been documented, that there have been cases of ICDs attempting to deliver as many as hundreds of subclinical shocks while in an MRI environment. In this case, the ICD senses a chaotic heart rhythm, however, due to the saturation of the ferrite element(s), the ICD energy storage capacitor is only charged to a relatively low voltage. Accordingly, it can only deliver low energy shocks that are generally subclinical (below 5 joules). In fact, there have been cases of the ICD attempting to deliver so many shocks that it depletes its own battery before the MRI scan is even completed.

Accordingly, what is needed is a design and methodology wherein the ICD can deliver a therapeutic cardioversion and/or defibrillation shock while in the presence of the MRI main static field ($B_0$). This is particularly important for a patient at risk for dangerous ventricular arrhythmias. In addition, the MRI environment can be a very stressful environment for many patients. Anxiety is a well documented phenomenon for patients who become claustrophobic while placed into the relatively small diameter bore of the MRI scanner. These stress levels are particularly high in so-called "closed-bore" scanners. In a high risk patient, the chance for a dangerous arrhythmia increases when the patient is in the MRI bore. The present invention fulfills these needs and provides other related advantages.

SUMMARY OF THE INVENTION

An exemplary embodiment of an implantable cardioverter defibrillator (ICD) is disclosed including a hermetically sealed housing and a communication interface disposed within the housing operable to receive a communication signal from an external programmer. The communication signal includes a command to switch the implantable cardioverter defibrillator from a first mode to a second mode. A processor is disposed within the housing in electrical communication with the communication interface. The processor is configured to switch the implantable cardioverter defibrillator between the first and second modes. A battery is disposed within the ICD housing configured to convert chemical energy into electrical energy at a relatively low DC voltage. A DC to AC converter is disposed within the housing electrically coupled to the battery and configured to convert the low DC voltage to a low AC voltage. A transformer is disposed within the housing electrically coupled to the converter configured to convert the low AC voltage to a high AC voltage. A rectifier is disposed within the housing electrically coupled to the transformer and configured to convert the high AC voltage to a high DC voltage. An energy storage capacitor, which is used to store and deliver the necessary defibrillation energy, is disposed within the housing electrically coupled to the rectifier, wherein the energy storage capacitor is configured to store the defibrillation energy at a high DC voltage. The defibrillation energy may comprise at least 10 joules. A high voltage switch is disposed within the housing electrically coupled to the energy storage capacitor. A bleed off circuit is disposed within the housing electrically coupled to the energy storage capacitor. An optional timer is in electrical communication with the processor operable to measure a period of time of the second mode, wherein the processor is configured to switch the implantable cardioverter defibrillator from the second mode to the first mode after the period of time has elapsed and activate the bleed off circuit to dissipate the energy. Alternately, the energy may be allowed to self discharge or bleed-off, without the use of the bleed-off or dump resistor. It is also a feature of the present invention that the switching from the first to the second mode and then from the second mode back to the first mode can all be done by use of an external programmer and programming commands communicated through the ICD's telemetry circuits. The second mode includes activating the DC to AC converter, transformer and rectifier to change the low DC voltage to the high DC voltage and stored energy within the energy storage capacitor during the period of time of the second mode. The implantable cardioverter defibrillator can now deliver a therapeutic cardioversion or defibrillation shock while in the presence of an MRI field.

In exemplary embodiments, the period of time of the second mode may include more than 20 minutes. Other periods of time are possible such as 30, 40, 50 or 60 minutes. The energy stored may be at least 10, 20, 30, 40 or 50 joules. The amount of effective defibrillation energy stored can vary widely based on the voltage of the capacitors, the type of therapy being delivered, electrode location within the heart, discharge pathway resistance within the heart, etc.

In another exemplary embodiment, an additional variation of a secondary mode could be such that the defibrillator device contains a magnetic field sensor which detects the $B_0$ field such that in the absence of the $B_0$ field, the secondary mode is automatically terminated.

Another exemplary embodiment of an implantable medical device includes a hermetically sealed housing and a communication interface disposed within the housing operable to receive a communication signal from an external programmer. The communication signal includes a command to switch the implantable medical device from a first mode to a second mode. A processor is disposed within the housing in electrical communication with the communication interface. While at a suitable distance from the MRI scanner or bore, the processor is configured to switch the implantable medical device between the first and second modes. A battery is disposed within the housing to supply a low DC voltage. A converter is disposed within the housing configured to convert the low DC voltage to a high DC voltage. An energy storage capacitor is disposed within the housing electrically coupled to the converter, wherein the energy storage capacitor is configured to store the high DC voltage at the effective defibrillation energy. The second mode includes activating the converter to convert the low DC voltage to the high DC voltage and storing the effective defibrillation energy in the energy storage capacitor during a period of time of the second mode. The implantable cardioverter defibrillator can now deliver a therapeutic cardioversion or defibrillation shock while in the presence of an MRI field.

In exemplary embodiments, the converter may include a DC to AC converter disposed within the housing electrically coupled to the battery and configured to convert the low DC voltage to a low AC voltage. The converter may include a transformer disposed within the housing electrically coupled to the DC to AC converter configured to convert the low AC voltage to a high AC voltage. The converter may include a rectifier disposed within the housing electrically coupled to the transformer and configured to convert the high AC voltage to the high DC voltage.

A high voltage switch may be disposed within the housing electrically coupled to the energy storage capacitor.

A bleed off circuit may be disposed within the housing electrically coupled to the energy storage capacitor. The processor may activate the bleed off circuit to dissipate the effective defibrillation energy when switching the second mode to the first mode. The period of time of the second mode may include more than 20 minutes. Alternatively, the period of time of the second mode may include 25, 30, 35, 40, 45, 50, 55 or 60 minutes.

A timer may be in electrical communication with the processor operable to measure the period of time of the second mode, wherein the processor is configured to switch the implantable medical device from the second mode to the first mode after the period of time has elapsed.

The communication interface may be operable to receive a second communication signal from an external programmer, wherein the second communication signal comprises a command to switch the implantable medical device from the second mode to the first mode.

Another exemplary embodiment of an implantable medical device includes a communication interface operable to receive a communication signal from an external programmer, wherein the communication signal comprises a command to switch the implantable medical device from a first mode to a second mode. A processor is in electrical communication with the communication interface, the processor configured to switch the implantable medical device between the first and second modes. A battery is configured to supply a low DC voltage. A converter is configured to convert the low DC voltage to a high DC voltage. A energy storage capacitor is electrically coupled to the converter, wherein the energy storage capacitor is configured to store the effective defibrillation energy at the high DC voltage. The second mode includes activating the converter to convert the low DC voltage to the high DC voltage and storing the effective defibrillation energy within the energy storage capacitor during a period of time of the second mode.

In exemplary embodiments the converter may include a DC to AC converter electrically coupled to the battery and configured to convert the low DC voltage to a low AC voltage. The converter may comprise a switch mode power supply (SMPS). The converter may include a transformer electrically coupled to the DC to AC converter configured to convert the low AC voltage to a high AC voltage. The converter may include a rectifier electrically coupled to the transformer and configured to convert the high AC voltage to the high DC voltage.

A high voltage switch may be electrically coupled to the high energy storage capacitor.

A bleed off circuit may be electrically coupled to the high energy storage capacitor, wherein the processor activates the bleed off circuit to dissipate the remaining stored energy when switching the second mode to the first mode. The period of time of the second mode may include more than 20 minutes.

A timer may be in electrical communication with the processor operable to measure a period of time of the second mode, wherein the processor is configured to switch the implantable medical device from the second mode to the first mode after the period of time has elapsed.

In another exemplary embodiment, an additional variation of a secondary mode could be such that the defibrillator device contains a magnetic field sensor which detects the $B_0$ field such that in the absence of the $B_0$ field, the secondary mode is automatically terminated.

The communication interface may be operable to receive a second communication signal from an external programmer, wherein the second communication signal comprises a command to switch the implantable medical device from the second mode to the first mode.

The external programmer may include a self-contained hand-held device operable to switch the implantable medical device between the first and second modes. The hand-held device may include a display indicating the mode of the implantable medical device. The hand-held device may include a first button (or a touch screen operable icon) operable to switch the implantable medical device from the first mode to the second mode. The hand-held device may include a second button (or touch screen operable icon) operable to switch the implantable medical device from the second mode to the first mode.

Another exemplary embodiment of the present invention includes a method of performing a magnetic resonance imaging (MRI) scan on a patient with an implanted cardioverter defibrillator (ICD). The method includes sending a communication signal from an external programmer to the ICD absent a presence of an MRI field generated by an MRI scanner, the communication signal comprising a command to charge a energy capacitor of the ICD before the patient undergoes the MRI scan; moving the patient in close proximity to the MRI scanner; performing the MRI scan; removing the patient from the MRI scanner when the MRI scan is completed or when the ICD delivers a therapy or defibrillation shock while in the presence of the MRI field; moving the patient substantially away from the MRI field; and allowing the ICD to either automatically bleed off, or self-discharge, the remaining stored energy in the capacitor (or after completing the MRI scan, or, allowing the ICD to recharge the energy capacitor and deliver a second therapeutic charge or defibrillation shock to the patient.

The method may also include the step of monitoring the status of the patient or ICD while performing the MRI scan, wherein monitoring the status of the patient may include monitoring EKG or pulse ox of the patient.

The method may also include the step of sounding an alarm for emergency personnel when the ICD delivers the therapeutic charge or defibrillation shock.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Various types of active implantable medical devices are currently in use. For example, a family of implantable hearing devices can include the group of cochlear implants, piezoelectric sound bridge transducers and the like. Additionally, neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. Cardiac pacemakers are well-known in the art such as left ventricular assist devices (LVAD's), and artificial hearts, including the recently introduced artificial heart known as the Abiocor. Additionally, an entire family of drug pumps can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted leadwires. Additionally, implantable bone growth stimulators for rapid healing of fractures are possible along with urinary incontinence devices. Additionally, pain relief spinal cord stimulators, anti-tremor stimulators, and other types of neurostimulators used to block pain are possible. It is also possible for one to have an externally worn pack. This pack could be an external insulin pump, an external drug pump, an external neurostimulator or even a ventricular assist device.

Figure 1:
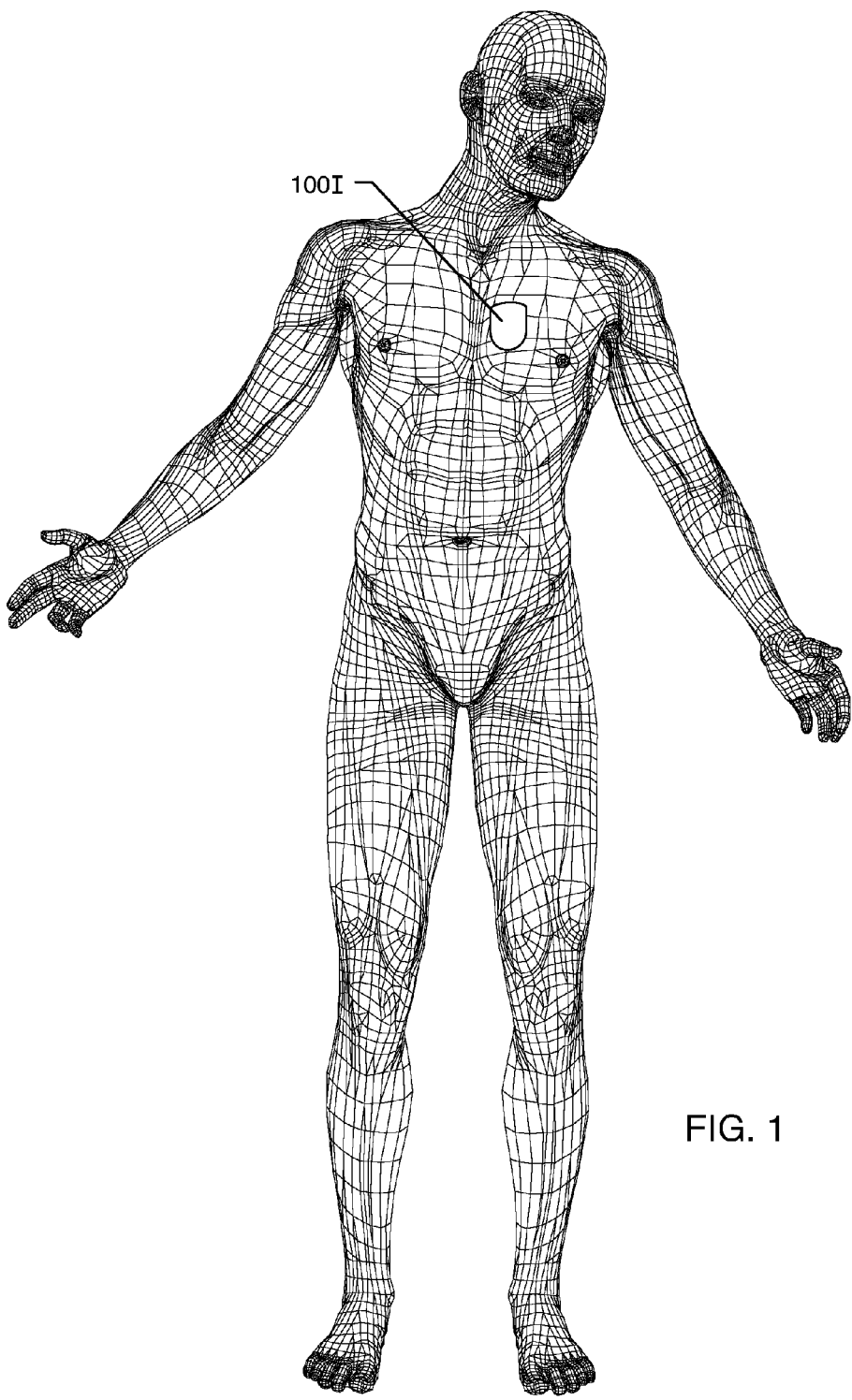
FIG. 1 illustrates a wire-formed diagram of a generic human body showing an exemplary implanted cardioverter defibrillator.

FIG. 1 illustrates a wire-formed diagram of a generic human body showing an exemplary implanted cardioverter defibrillator 100I. Numerical designation 100I includes a family of implantable cardioverter defibrillator (ICD) devices and also includes the family of congestive heart failure devices (CRT-D). This is also known in the art as cardio resynchronization therapy devices, otherwise known as CRT-D devices.

Referring to U.S. 2003/0050557, the contents of which are incorporated herein by reference, metallic structures, particularly leads, are described that when placed in MRI scanners, can pick up high electrical fields which results in local tissue heating. This heating tends to be most concentrated at the ends of the electrical structure (either at the proximal or distal lead ends). A significant concern is that the distal electrodes, which are in contact with body tissue, can cause local tissue burns.

As used herein, the lead means an implanted lead, including its conductors and electrodes that have electrodes that are in contact with body tissue. In general, for an active implantable medical device (AIMD), the term lead means the lead that is outside of the AIMD housing and is implanted or directed into body tissues. The term leadwire as used herein refers to the wiring or circuit traces that are generally inside of the AIMD and are not exposed directly to body fluids.

Figure 2:
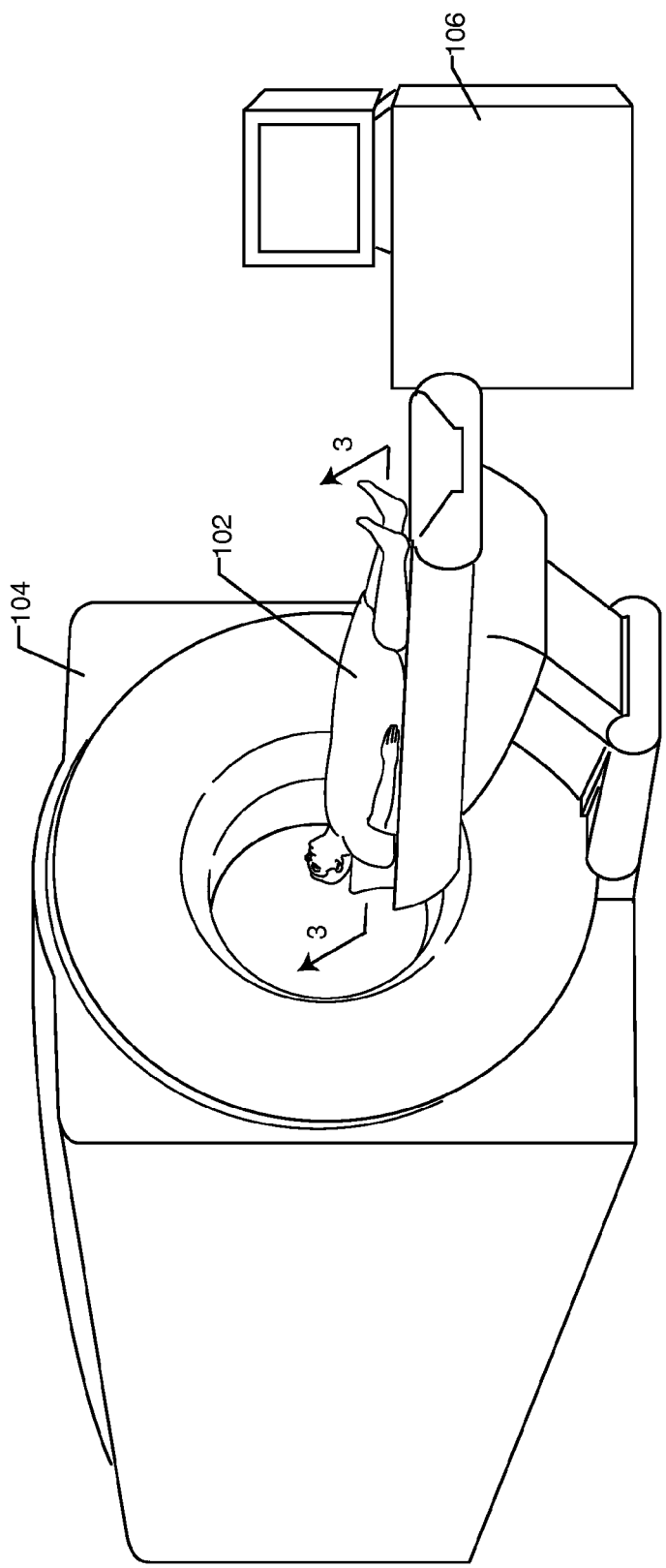
FIG. 2 illustrates a perspective view of an AIMD patient who is about to be placed into an MRI scanner.

FIG. 2 illustrates an AIMD patient 102 about to be conveyored into an MRI machine 104. Imaging processing equipment is shown as 106. The static field of the MR scanner saturates ferromagnetic components within the ICD100I. As will be shown, the ICD high energy storage capacitor would be unable to charge up to a high voltage level because of the saturation of the ICD high voltage transformer. This means the patient 102 is without the benefit of the ICD100I while in the presence of the MRI machine 104. Furthermore, the MRI machine 104 may actually cause the ICD to completely deplete its battery, thereby requiring surgery to replace the old ICD with a new ICD100I.

Figure 3:
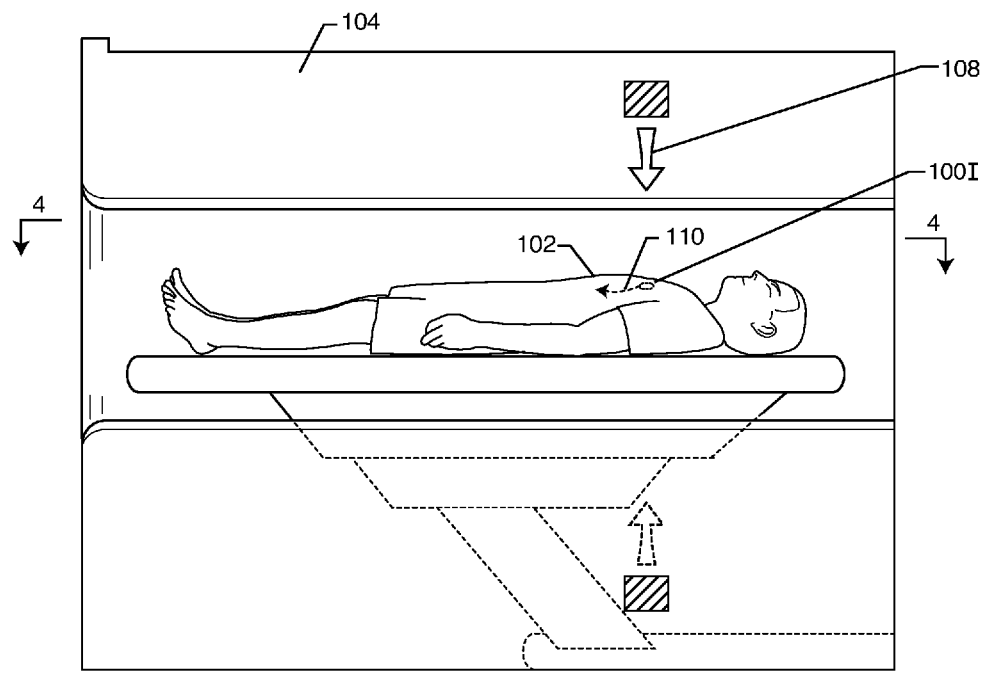
FIG. 3 illustrates a side view of the patient within the scanner showing an intense RF field impinging on the implanted cardioverter defibrillator and its associated lead.

FIG. 3 is a side view showing the patient 102 within the MRI scanner bore 104. An intense static $B_0$ field 114 is generated by the scanners cryogenic magnets. As can be seen, this static field 114 is impinging on both the implanted cardioverter defibrillator 100I and its associated leads 110. ICDs 100I are typically implanted in either the right or the left part of the chest in a pectoral pocket. In some cases, they can be implanted abdominally.

Figure 4:
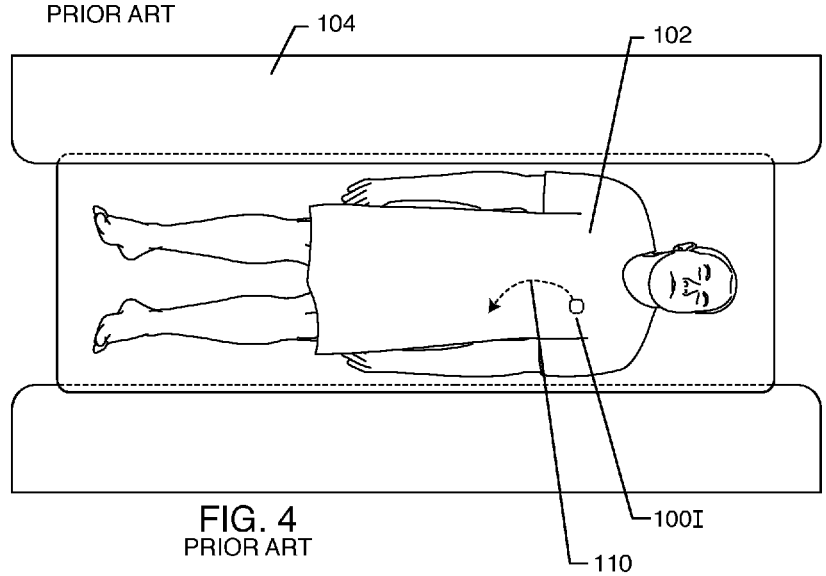
FIG. 4 illustrates a top view of the patient in the MRI scanner showing one location of the implantable cardioverter defibrillator and its associated lead.

FIG. 4 is a top view of the patient 102 inside the MRI scanner bore 104. As can be seen, the ICD100I is in a left pectoral pocket with the leads 110 routed transvenously down into the interior chambers of the heart.

Figure 5:
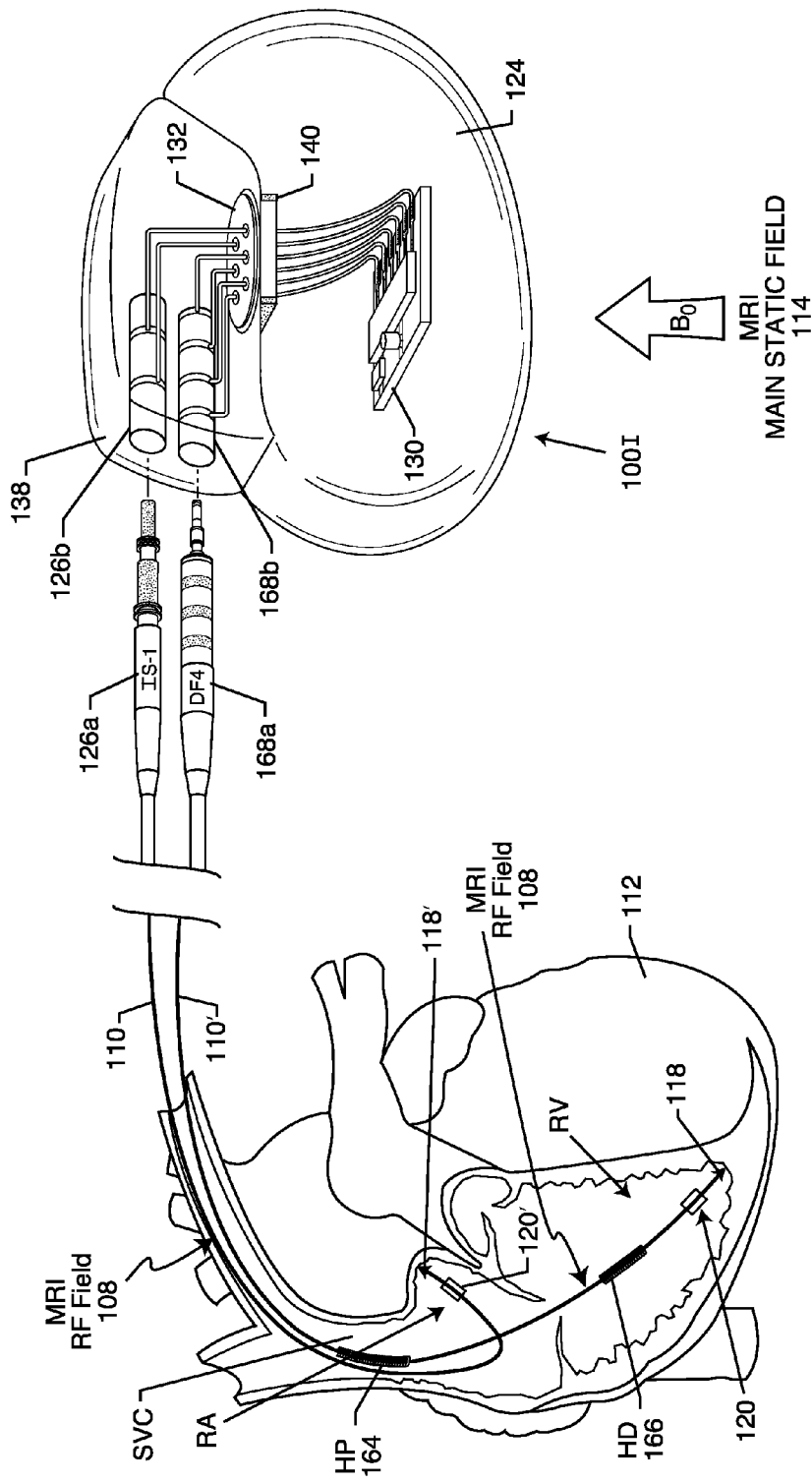
FIG. 5 illustrates a pictorial view of a dual chamber cardiac pacemaker with its associated leads and electrodes.

FIG. 5 illustrates a pictorial view of a dual chamber ICD100I showing a bipolar IS-1 lead 110 routed from the ICD100I to a bipolar tip electrode 118' and anode ring electrode 120' located inside the right atrium. In addition, there is one of the new inline quadripolar connectors DF4 shown routed to implanted lead 110'. Lead 110' is routed to two high voltage shocking coils HP, 164 and HD, 166. Shocking coil HP is located in the superior vena cava while shocking coil HD is located in the right ventricle. Referring once again to the DF4 connector, it also has two (bipolar) low voltage lead conductors which are routed to the bipolar electrodes 118 and 120 which are located inside of the right ventricle (RV). As can be seen, the implanted leads 110 and 110' are exposed along their length to the intense MRI RF-pulsed field 108. In addition, the ICD 100I and all of its electronics are directly exposed to the MRI main static field 114. Typically, this is either 1.5 T or 3 T. As previously described, this powerful main static field $B_0$ saturates ferrule magnetic components, such as a ferrite or iron based transformer (not shown). Referring once again to FIG. 5, one can see that there is a feedthrough capacitor-type EMI filter 140 adjacent the hermetic seal. The feedthrough capacitor 140 decouples high frequency energy, such as the MRI RF-pulsed frequency 108 where such energy is diverted to the housing 124 of the ICD100I. This feedthrough capacitor is important in the present invention in that the ICD high energy storage capacitor 140 will be previously charged outside of the MRI environment. It is very important that the ICD100I not inadvertently sense the MRI RF-pulsed field 108 as a chaotic or dangerous ventricular arrhythmia. In this case, if the ICD100I falsely sensed the MRI RF or gradient field as EMI, it would inappropriately deliver the high energy shock to the patient 102. Accordingly, proper EMI filtering is essential in the present invention to remove the carrier of the RF-pulsed field 108 such that it cannot cause inappropriate sensing. Referring once again to FIG. 5, the hermetic seal assembly 132 is generally comprised of a gold brazed alumina insulator, a glass-to-metal seal, or the like. Typically, it will have a ferrule 134 (not shown), which is laser welded directly to the ICD housing 124. This creates a hermetic seal, which protects all ICD electronic circuits from body fluid intrusion.

FIGS. 6-10 illustrate a prior art rectangular hexpolar feedthrough capacitor (planar array) 140 mounted to the hermetic terminal 132 of an ICD in accordance with U.S. Pat. No. 5,333,095 to Stevenson et al. the contents of which are incorporated herein. As illustrated in FIGS. 6-10, in a typical broadband or lowpass EMI filter construction, a ceramic feedthrough filter capacitor 140 is used in a hermetic feedthrough assembly 132 to suppress and decouple undesired interference or noise transmission along one or more terminal pins 142, and may comprise a capacitor having two sets of electrode plates 144 (six active electrode plate) and 146 (three ground electrode plates) embedded in spaced relation within an insulative dielectric substrate or base 148, formed typically as a ceramic monolithic structure. One set of the active electrode plates 144 is electrically connected at an inner diameter cylindrical surface of the capacitor structure 140 to the conductive terminal pins 142 utilized to pass the desired electrical signal or signals. The other or second set of ground electrode plates 146 is coupled at an outer edge surface 150 of the capacitor 140 through metallization to a rectangular ferrule 134 of conductive material. In the prior art, without regard to high frequency capacitor ESR, the number and dielectric thickness spacing of the electrode plate sets 144, 146 varies in accordance with the capacitance value and the voltage rating of the capacitor 140.

In operation, the capacitor 140 permits passage of relatively low frequency electrical signals along the terminal pins 142, while shielding and decoupling/attenuating undesired interference signals of typically high frequency to the conductive housing 124. Feedthrough capacitors 140 of this general type are available in unipolar (one), bipolar (two), tripolar (three), quadpolar (four), pentapolar (five), hexpolar (6) and additional lead configurations. Feedthrough capacitors 140 (in both discoidal and rectangular configurations) of this general type are commonly employed in implantable cardiac pacemakers and defibrillators and the like, wherein the pacemaker/ICD housing is constructed from a biocompatible metal such as titanium alloy, which is electrically and mechanically coupled to the hermetic terminal pin assembly which is in turn electrically coupled to the coaxial feedthrough filter capacitor 140. As a result, the filter capacitor and terminal pin assembly prevents entrance of interference signals to the interior of the pacemaker/ICD housing 124, wherein such interference signals could otherwise adversely affect the desired cardiac pacing or defibrillation function.

Figure 6:
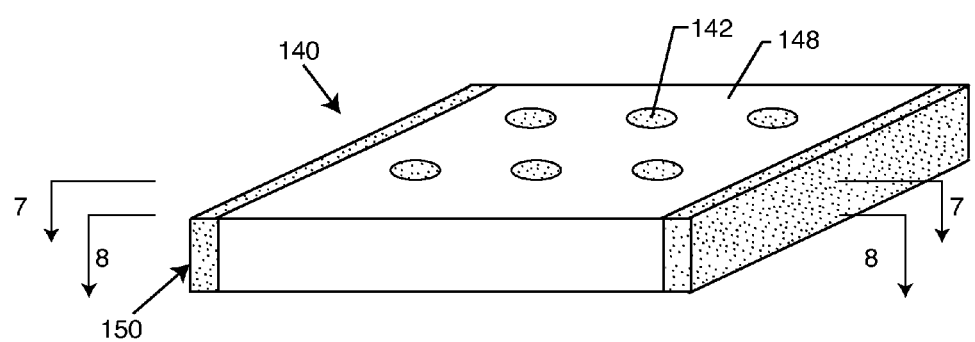
FIG. 6 illustrates a perspective view of a rectangular broadband or lowpass EMI filter capacitor.
Figure 7:
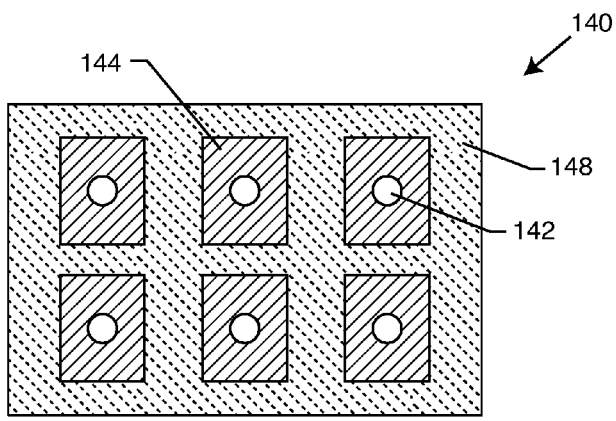
FIG. 7 illustrates a horizontal section taken generally along the line 7-7 of FIG. 6, illustrating the configuration of active electrode plates within the rectangular capacitor.

FIG. 7 illustrates a horizontal section taken generally along the line 7-7 of FIG. 6, illustrating the configuration of active electrode plates 144 within the rectangular capacitor 140.

Figure 8:
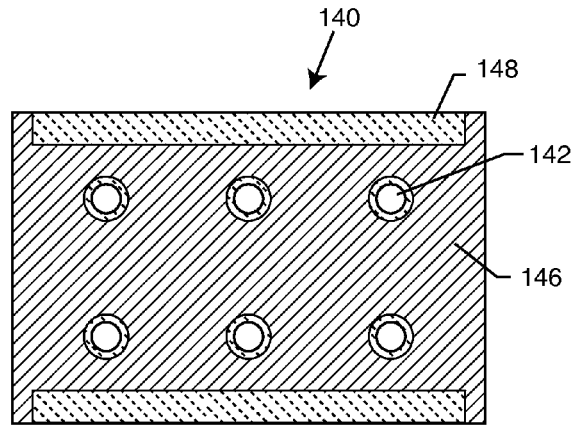
FIG. 8 illustrates a horizontal section taken generally along the lines 8-8 of FIG. 6, illustrating the configuration of ground electrode plates within the rectangular capacitor.

FIG. 8 illustrates a horizontal section taken generally along the lines 8-8 of FIG. 6, illustrating the configuration of ground electrode plates 146 within the rectangular capacitor 140.

Figure 9:
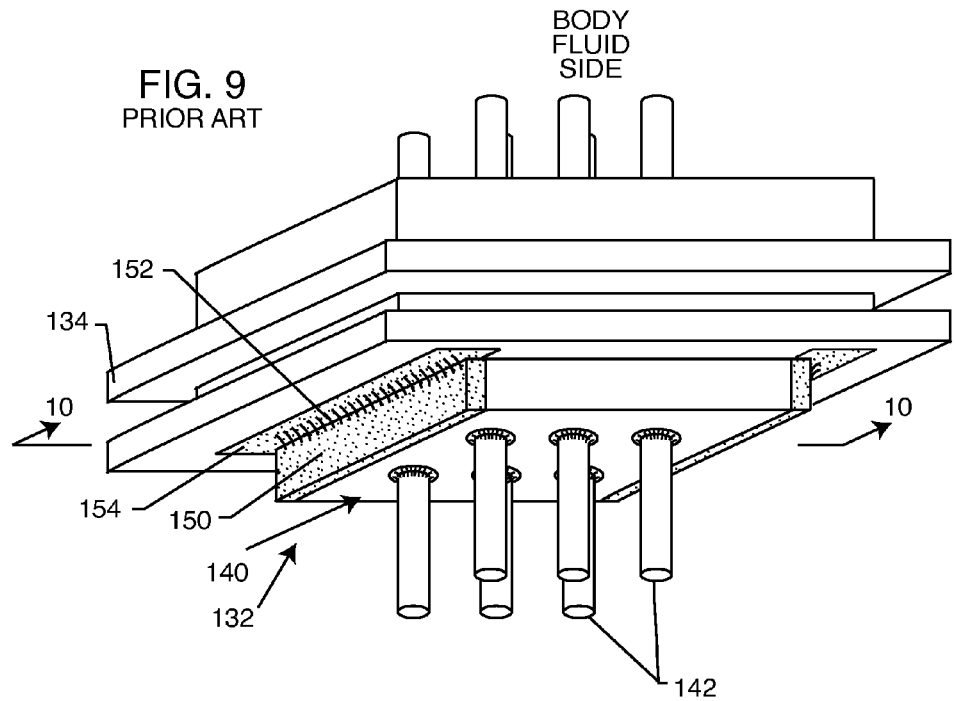
FIG. 9 illustrates a perspective view showing the rectangular feedthrough capacitor of FIG. 6 mounted to a hermetic terminal.

FIG. 9 shows a hexpolar feedthrough capacitor 140 (which is identical to the capacitor of FIG. 6) mounted to the hermetic terminal 132 of FIG. 5. As one can see in FIG. 9, the conductive polyimide material 152 now connects between the capacitor metallization 150 and the gold braze area 154. The gold braze 154 forms a metallurgical bond with the titanium and precludes any possibility of an unstable oxide forming. Gold is a noble metal that does not oxidize and remains very stable even at elevated temperatures. The construction methodology illustrated in FIG. 9 guarantees that the capacitor ohmic losses will remain very small at all frequencies. By connecting the capacitor's electrode plates 146 to a low resistivity surface such as gold, one is guaranteed that this connection will not substantially contribute to the capacitor's overall ESR. Keeping the ESR as low as possible is very important for diverting a high amount of RF current such as that induced in the lead system by MRI scanners. One is referred to U.S. Pat. No. 6,765,779 to Stevenson et al., for additional information on electrically connecting to non-oxidized surfaces, the contents of which are incorporated herein by reference.

Figure 10:
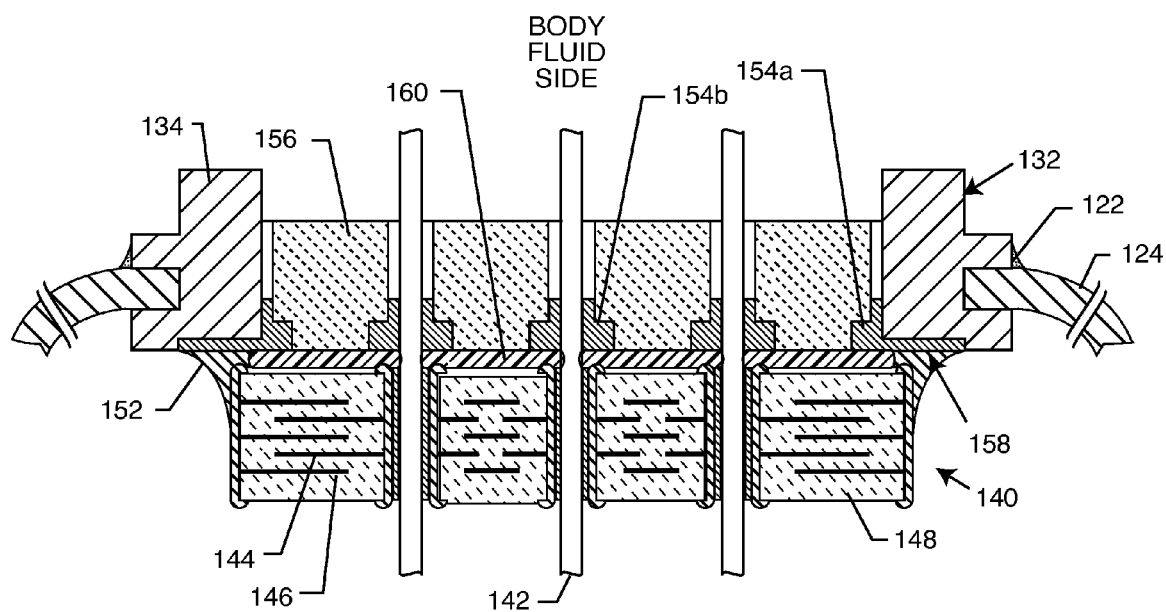
FIG. 10 illustrates a sectional view of the structure of FIG. 9 taken generally along the line 10-10.

FIG. 10 is a cross-section of the capacitor 140 shown in FIG. 9. One can see that the gold braze (or weld) areas 154a and 154b that form the hermetic seal between an alumina insulator 156 and the titanium ferrule 134 are desirably on the feedthrough capacitor side. This makes it easy to manufacture the gold bond pad area 158 for convenient attachment of the conductive thermal-setting material 152. In other words, by having the gold braze hermetic seals 154 on the same side as the gold bond pad area 158, these can be co-formed in one manufacturing operation in a gold braze vacuum furnace. Further, a unique thermal-setting material 160 is disposed between the capacitor 140 and the underlying hermetic terminal 132. A laser weld 122 is formed continuously about the ferrule 132 to form a hermetic seal to the ICD housing 124. Importantly, this laser weld 122 also insures that the feedthrough capacitor 140 will comprise a continuous electromagnetic shield in order to prevent interference to sensitive ICD electronic circuits.

Figure 11:
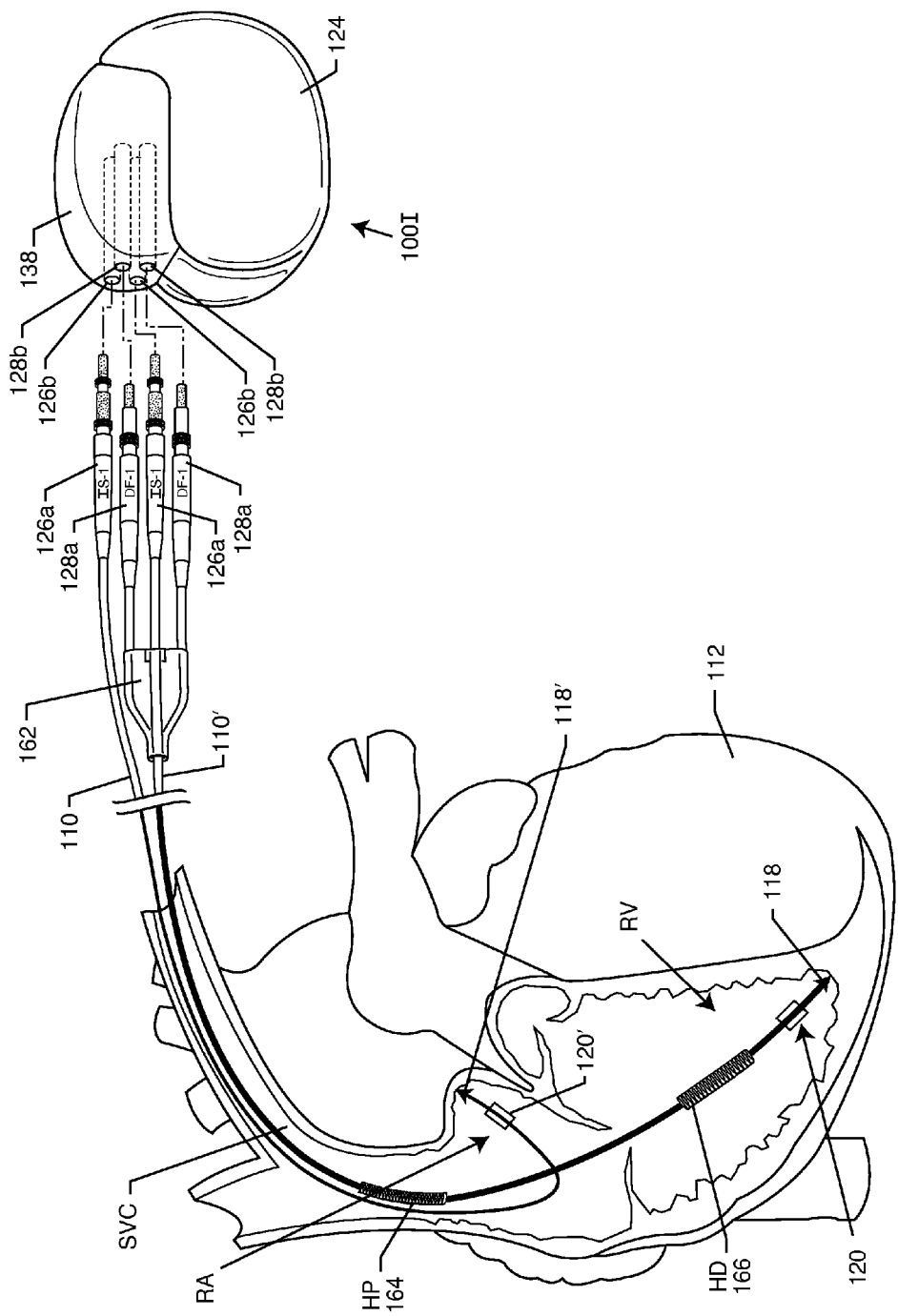
FIG. 11 illustrates a pictorial view of a prior art dual chamber implantable cardioverter defibrillator with leads and shocking coils implanted into a human heart showing the complex trifurcated connector on the quadripolar ventricular lead.

FIG. 11 illustrates a pictorial view of an old-style prior art dual chamber implantable cardioverter defibrillator 100I with leads and shocking coils implanted into a human heart 112 showing the complex trifurcated connector 162 on the quadripolar ventricular lead. In FIG. 11, one can see that there is a trifurcated lead adaptor 162 which combines the connectors 128a for the two high-voltage shocking coils 164, 166 along with a bipolar low-voltage tip electrode 118 and ring electrode 120 with connector 126a. The connectors 128a go into connector cavities 128b. Referring once again to FIG. 11, one can see that there is also a bipolar IS-1 connector 126a which is routed to a tip electrode 118' and a ring electrode 120' in the right atrium (RA). In the prior art, excess lead is typically wound up in the pectoral pocket, either adjacent to or around the pacemaker/ICD and makes for a very bulky pectoral pocket lead arrangement as compared to the arrangement shown in FIG. 12. In addition the four separate connectors and associated proximal lead segments tend to create criss-crossing tissue in-growth paths. When the ICD100I needs to be replaced for approaching battery end of life or any other indication, the tangle of insulated conductor segments all tend to have tissue in-growth which makes the surgery difficult as all of the leads must be carefully excised and separated.

Figure 12:
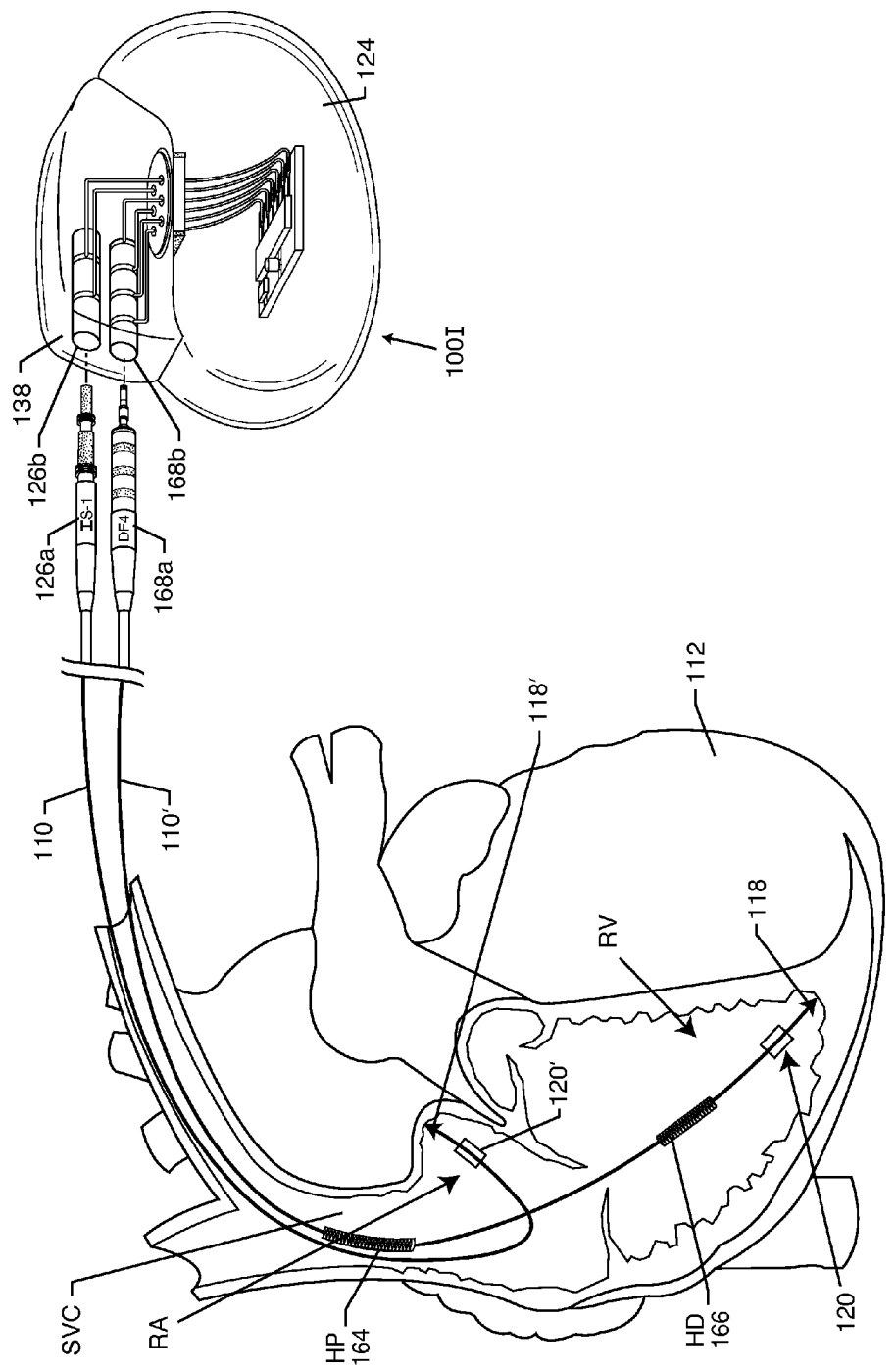
FIG. 12 illustrates a pictorial view of a state-of-the-art dual chamber implantable defibrillator similar to FIG. 11 but now with the new in-line DF4 quadpolar connector replacing the prior cumbersome trifurcated lead based adaptor.

FIG. 12 illustrates a pictorial view of a state-of-the-art dual chamber implantable defibrillator 100I similar to FIG. 11, but now with the new in-line DF4 quadripolar connector 168 replacing the prior cumbersome trifurcated lead based adaptor 162. As illustrated in FIG. 11, the dual chamber ICD100I has both a pacing and high-voltage shocking functions. The electrode placements, both for the high-voltage shocking coils and also the low voltage pacing sense circuits are the same as previously described for FIG. 11. However, in FIG. 12, the defibrillator 100I lead 110' incorporates the new state-of-the-art inline quadripolar DF4 proximal lead connector 168a as shown. In this case, there are now only two connector cavities 168b and 126b in the defibrillator 100I header 138. Connector cavity 126b is a low-voltage bipolar connector cavity for receipt of the IS-1 proximal connector 126a. Connector cavity 168b is a DF4 quadripolar connector cavity designed to receive the DF4 proximal connector 168a. In this case, there are still two leads 110 and 110' that are routed down into the various chambers of the heart as previously described in FIG. 11. When one considers the excess lead is would up in the pacemaker pocket, one can see that the configuration in FIG. 12 is vastly superior to the trifurcated connector 134 as previously illustrated in FIG. 11. The surgical implant procedure is considerably simplified and there is a lot less bulk created in the pacemaker pocket which increases both reliability and patient comfort.

Compatibility of cardiac pacemakers, implantable defibrillators and other types of active implantable medical devices with magnetic resonance imaging (MRI) and other types of hospital diagnostic equipment has become a major issue. If one proceeds to the websites of the major cardiac pacemaker manufacturers in the United States, which include St. Jude Medical, Medtronic and Boston Scientific (formerly Guidant), one will see that the use of MRI is generally contraindicated for patients with implanted pacemakers and cardioverter defibrillators. See also recent press announcements of the Medtronic Revo MRI pacemaker which was recently approved by the U.S. FDA. See the articles below which are all incorporated herein by reference:

(1) Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "1. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, Patent Application Publication US 2003/0050557, Susil and Halperin et al., published Mar. 13, 2003;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Pat. No. 7,844,534, Susil et al., issued Nov. 30, 2010.

However, an extensive review of the literature indicates that, despite being contra-indicated, MRI is indeed often used to image patients with pacemaker, neurostimulator and other active implantable medical devices (AIMDs). As such, the safety and feasibility of MRI in patients with cardiac pacemakers is an issue of gaining significance. The effects of MRI on patients' pacemaker systems have only been analyzed retrospectively in some case reports. There are a number of papers that indicate that MRI on new generation pacemakers can be conducted up to 0.5 Tesla (T). MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker or neurostimulator patients means that these patients are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AIMDs after an MRI procedure sometimes occurring many days later. Moreover, there are a number of recent papers that indicate that the SAR level is not entirely predictive of the heating that would be found in implanted leads or devices. For example, for magnetic resonance imaging devices operating at the same magnetic field strength and also at the same SAR level, considerable variations have been found relative to heating of implanted leads. It is speculated that SAR level alone is not a good predictor of whether or not an implanted device or its associated lead system will overheat.

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 5 Tesla. At the International Society for Magnetic Resonance in Medicine (ISMRM), which was held on 5-6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and/or lead systems. It is not likely (other than sudden system shut down) that the static MRI magnetic field can induce currents into the pacemaker lead system and hence into the pacemaker itself. It is a basic principle of physics that a magnetic field must either be time-varying as it cuts across the conductor, or the conductor itself must move within a specifically varying magnetic field for currents to be induced.

The second type of field produced by magnetic resonance imaging is the pulsed RF field which is generated by the body coil or head coil. This is used to change the energy state of the protons and elicit MRI signals from tissue. The RF field is homogeneous in the central region and has two main components: (1) the electric field is circularly polarized in the actual plane; and (2) the H field, sometimes generally referred to as the net magnetic field in matter, is related to the electric field by Maxwell's equations and is relatively uniform. In general, the RF field is switched on and off during measurements and usually has a frequency of about 21 MHz to about 500 MHz depending upon the static magnetic field strength. The frequency of the RF pulse for hydrogen scans varies by the Lamour equation with the field strength of the main static field where: RF PULSED FREQUENCY in MHz=(42.56) (STATIC FIELD STRENGTH IN TESLA). There are also phosphorous and other types of scanners wherein the Lamour equation would be different. The present invention applies to all such scanners.

The third type of electromagnetic field is the time-varying magnetic gradient fields designated $B_X$, $B_Y$, $B_Z$, which are used for spatial localization. These change their strength along different orientations and operating frequencies on the order of 2-5 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

Now turning to the present invention, these strong electromagnetic fields produced by MRI systems can cause problems for implantable medical devices and as a result, both the U.S. Food and Drug Administration (FDA) and many pacemaker manufacturers have issued warnings against pacemaker recipients undergoing MRIs. More specifically, it has been documented that implantable cardioverter defibrillators (ICDs) can exhibit a number of malfunctions when placed inside of a clinical MRI scanner bore. First of all, ICDs incorporate a high voltage power supply. This high voltage power supply converts the relatively low DC voltage from the ICD's internal battery to a high voltage DC that is required to charge up the ICD's high energy storage capacitor(s). Once the high energy storage capacitors of the ICD are charged up, they can then deliver a therapeutic shock (typically in the area of 32 to 40 joules). The internal ICD power supply (switch mode or other) does embody ferrite materials, such as a ferrite core transformer. In the presence of the main static $B_0$ field of the MR scanner, these ferrite materials saturate and become very inefficient. It has been documented, that the charging transformer of an ICD will saturate during an MRI scan thereby making it impossible to charge up the ICD's high energy storage capacitor to a high enough voltage level.

It has also been documented, that there have been cases of ICDs attempting to deliver as many as hundreds of subclinical shocks while in an MRI environment. In this case, the ICD senses a chaotic heart rhythm, however, due to the saturation of the ferrite element(s), the ICD energy storage capacitor is only charged to a relatively low voltage. Accordingly, it can only deliver low energy shocks that are generally subclinical (below 5 joules). In fact, there have been cases of the ICD attempting to deliver so many shocks that it depletes its own battery before the MRI scan is even completed.

Accordingly, the present invention embodies a design and methodology wherein the ICD can deliver a therapeutic cardioversion and/or defibrillation shock while in the presence of the MRI main static field ($B_0$). This is particularly important for a patient at risk for dangerous ventricular arrhythmias. In addition, the MRI environment can be a very stressful environment for many patients. Anxiety is a well documented phenomenon for patients who become claustrophobic while placed into the relatively small diameter bore of the MRI scanner. These stress levels are particularly high in so-called "closed-bore" scanners. In a high risk patient, the chance for a dangerous arrhythmia increases when the patient is in the MRI bore.

The present invention is particularly suited for use with an ICD which employs special input filtering such that the MRI RF pulsed field (B1) can't enter into the ICD electronics wherein electromagnetic interference (EMI) from such a field could be confused with an abnormal or dangerous ventricular arrhythmia such as ventricular fibrillation. These special filters help prevent an inappropriate ICD shock and are more thoroughly described in U.S. Pat. Nos. 7,751,903; 7,689,288 and in particular US 20100217262 (see FIG. 81 for example).

The present invention is based on ICD hardware, software and external programmer modifications in order to accomplish the following sequence:

1) The ICD is especially programmed while the patient is outside of the MR scanner bore such that the ICD's high energy storage capacitor is charged up. This is done prior to the patient entering the MRI bore so that the ICD circuit board ferrites and power supply transformer will work properly. The ICD is typically in a first mode, which is a mode with all of the program settings that the patient received at the time of implant or during a follow-up visit. Prior to entering an MRI suite, the patient is to be programmed into a second mode. This is a special MRI mode which can include many things, but in particular, it instructs the ICD to pre-charge the energy storage capacitor while still outside the bore. This programming can be done by either close coupled or distance RF prior art telemetry. In addition, a novel hand-held programmer of the present invention can be used. Typically, additional programming features would include turning off pacing sensor functions and therefore have the ICD100I pace both the ventricle via electrodes 118 and 120 and the atrium via electrodes 118' and 120' in an asynchronous mode (typically, this would be known in the industry as VOO), meaning that asynchronous pacing pulses at a predetermined rate in pulses per minute would continue throughout the entire time that the device was in its second mode. This is much safer in the presence of the fields of an MRI scanner in that, rate response features are turned off to minimize EMI effects.

2) Normal prior art circuitry within the ICD to bleed off the energy storage capacitor charge after a predetermined amount of time will be modified to allow a sufficient amount of time to complete the MRI scan. Typically the bleeder circuits will be disabled for between a 20 to 60 minute time frame. The predetermined amount of time can be preset during manufacture of the device or adjustable by the doctor/technician performing the MRI scan.

There are several ways in which the device can be programmed into a second mode and then returned to its first or normal operating mode. Three such means are (1) manually via a programmer, (2) via a timer or (3) through use of a magnetic field sensor. The first means would be to use an external programmer or hand-held device as previously described to place the ICD from a first mode into its second or MRI mode. The external programmer would similarly be used to place the ICD from the second mode back into the first mode. The second means would be where the device can be programmed with appropriate timing circuits so that it remains in an MRI mode for a specific period of time, at which time, it will automatically bleed off the stored high voltage energy and return to its first normal operating mode. As an alternative, the external programmer can be used to switch the device into its second mode and then at a later time, from its second operating mode back into its first operating mode in combination with a timer. In other words, this feature can be either automatic or manual. The third means would be through the use of a magnetic field sensor 218. The sensor 218 can be located within the ICD100I and formed as part of the electronic circuits 130 or as part of any other suitable electronic connection.

3) The patient will then enter the scan room and be placed in the MRI bore where the MRI scanning sequences will be performed. After the completion of the scans (assuming no defibrillation shock was delivered), the patient will be removed from the bore and the ICD energy shock capacitor may then be discharged and the ICD will be returned to its first mode normal programmed functions.

It is recognized that the patient will only be able to receive one life-saving cardioversion/defibrillation shock during the actual MRI scan. This is because, once the energy storage capacitor is discharged, it will not be possible to recharge it in the MRI bore because of the saturation of ferromagnetic materials (transformer) in the power supply circuitry. However, this is far better than having an ICD patient undergo a scan wherein the ICD is incapable of delivering any life-saving defibrillation shocks.

In a preferred embodiment, the energy storage capacitor will be charged to the desired defibrillation therapy voltage/energy prior to the initiation of the MRI scan. In other words, in a preferred embodiment, tiered shock therapies features will be turned off such that the patient can only receive the maximal shock. In the prior art, it's common to attempt to cardiovert or shock a patient at a lower voltage level to see if that lower voltage threshold will bring them back to normal sinus rhythm. One reason this is done, is that delivery of a high energy (~36 joules or higher) shock can be quite painful. However, because only one shock is available during the MRI scan, in the preferred embodiment, the highest energy shock available will be the preferred shock. In a preferred embodiment, the patient will be constantly monitored during the scan including an alarm if the ICD does deliver a high voltage therapy shock. At this point, the scan would be immediately terminated and the patient would be removed to a suitable distance away from the bore. Then, the ICD could, if necessary, re-charge its high energy capacitor so it could deliver additional life saving shocks if necessary.

Methods of placing the ICD into its "MRI mode" include: (1) reprogramming the device using an external programmer, or (2) using a special small programmer available to the MRI technician or radiologist (for example, a simple transmitter the size of a hand held garage door transmitter). Additional features can be programmed into the ICD to also prepare it for a safe MRI scan. For example, the ICD may have pacing functions.

In preparation for the MR scan, in addition to charging the energy storage capacitor, the pacing function of the ICD could be programmed to fixed rate (at a higher capture level), and non-sensing to minimize the possibility of EMI.

There are a number of patents in the prior art in which an active implantable medical device, such as a cardiac pacemaker is placed into an MRI "safe-mode" wherein circuitry within the pacemaker automatically detects the presence of the MRI main static field. These can be Hall effect sensors, reed switches or the like. In other words, when the pacemaker detects that it's in the presence of a huge magnetic field, it will reprogram itself typically into a fixed rate, non-sensing mode. This type of an approach will not work for the novel ICD of the present invention. The reason for that is, that by time the ICD detects that it's in the main static field or the MR scanner, the power supply ferrites will already be saturated and it will be unable to charge up its own internal energy storage capacitor. This is why preprogramming and pre-charging of the ICD's energy storage capacitor must be done before the patient comes in close proximity to the MRI scanner or even into the scan room.

Figure 13:
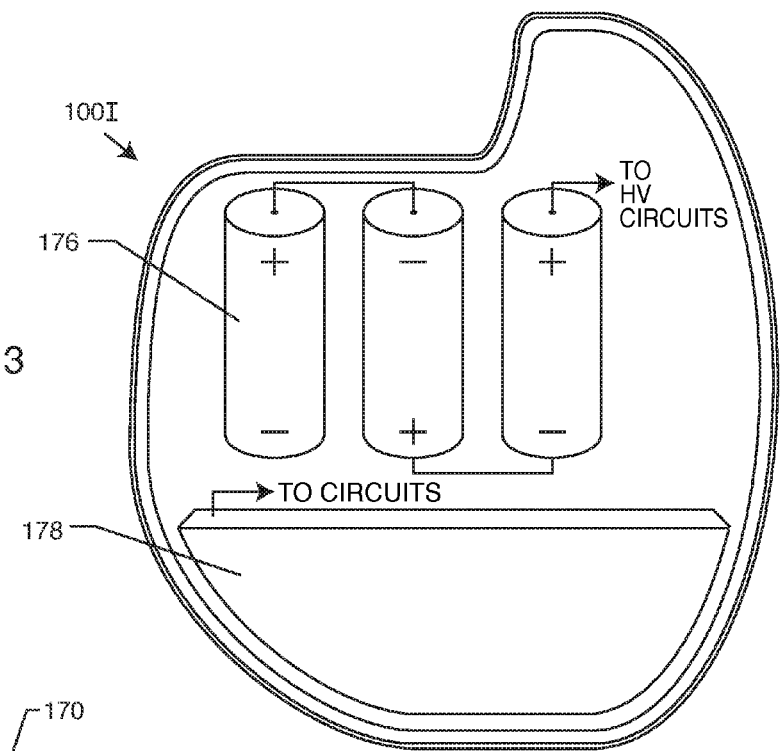
FIG. 13 illustrates an inside view of a first half of an implantable cardioverter defibrillator.

FIG. 13 illustrates an inside view of a first half of an implantable cardioverter defibrillator 100I. FIG. 3 also illustrates prior art energy storage capacitors 176. In this embodiment, they are wired in series to achieve a relatively high voltage (~200-800 volts). A low voltage battery 178 is also shown. It is not possible for the low voltage battery 178 to directly charge up the high voltage capacitors 176. This requires a DC to AC converter or SMPS 180, a transformer 172, and high voltage charging circuits 182 to accomplish. This involves a transformer 172 with a substantial amount of ferrite material.

Figure 14:
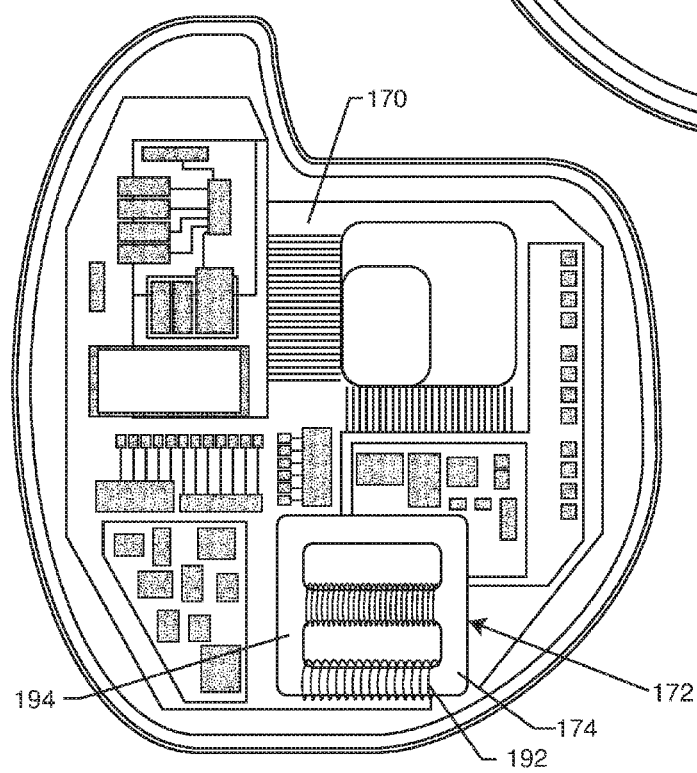
FIG. 14 illustrates an inside view of a second half of an implantable cardioverter defibrillator associated with the structure of FIG. 13.

FIG. 14 illustrates an inside view of a second half of an implantable cardioverter defibrillator 100I associated with the structure of FIG. 13. Shown are circuit boards and microprocessors 170. Also shown is the high voltage transformer 172 which one can see is wound around a ferrite or iron core 174. Ferromagnetic materials such as ferrite materials saturate in the presence of the main static field $B_0$ of the MR scanner 104 and become very inefficient. While in the presence of the main static field, the transformer 172 is unable to develop enough voltage to fully charge up the energy storage capacitor 176 from the battery 178 of the ICD100I. The result would be either no shock delivery or subclinical shock clinical delivery.

Figure 15:
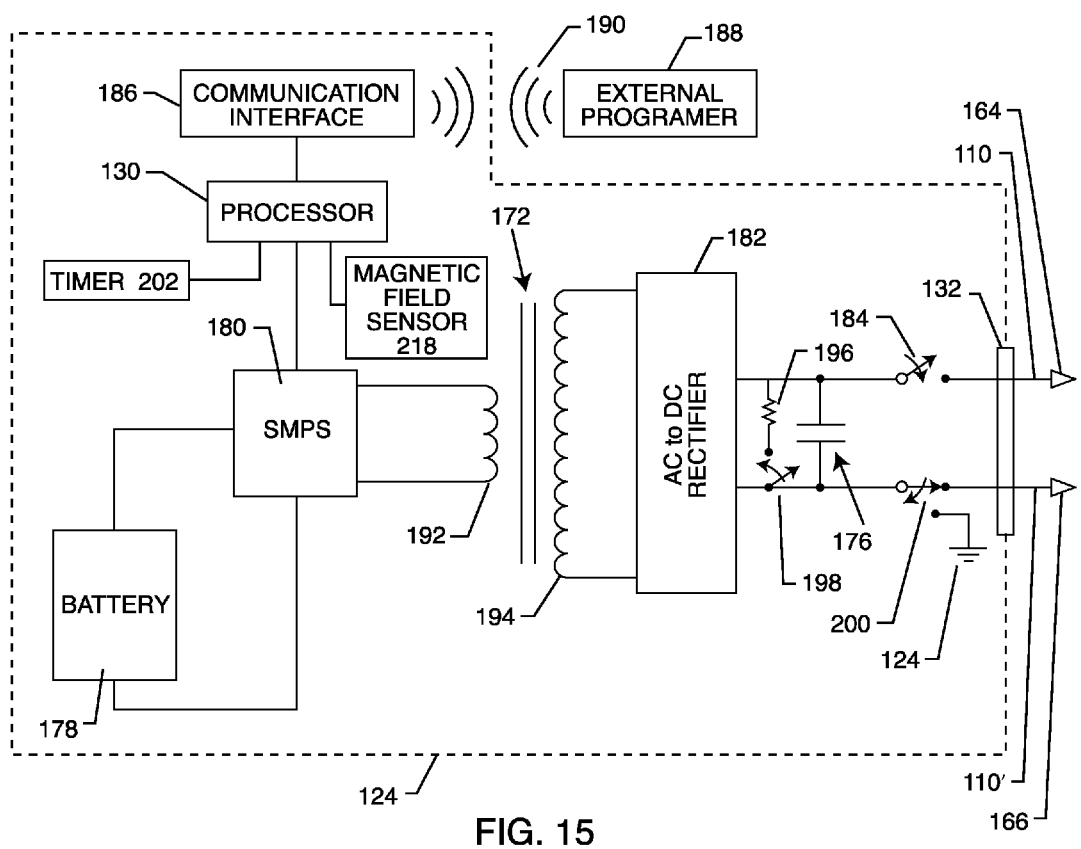
FIG. 15 illustrates an electrical schematic embodying the present invention.
Figure 17:
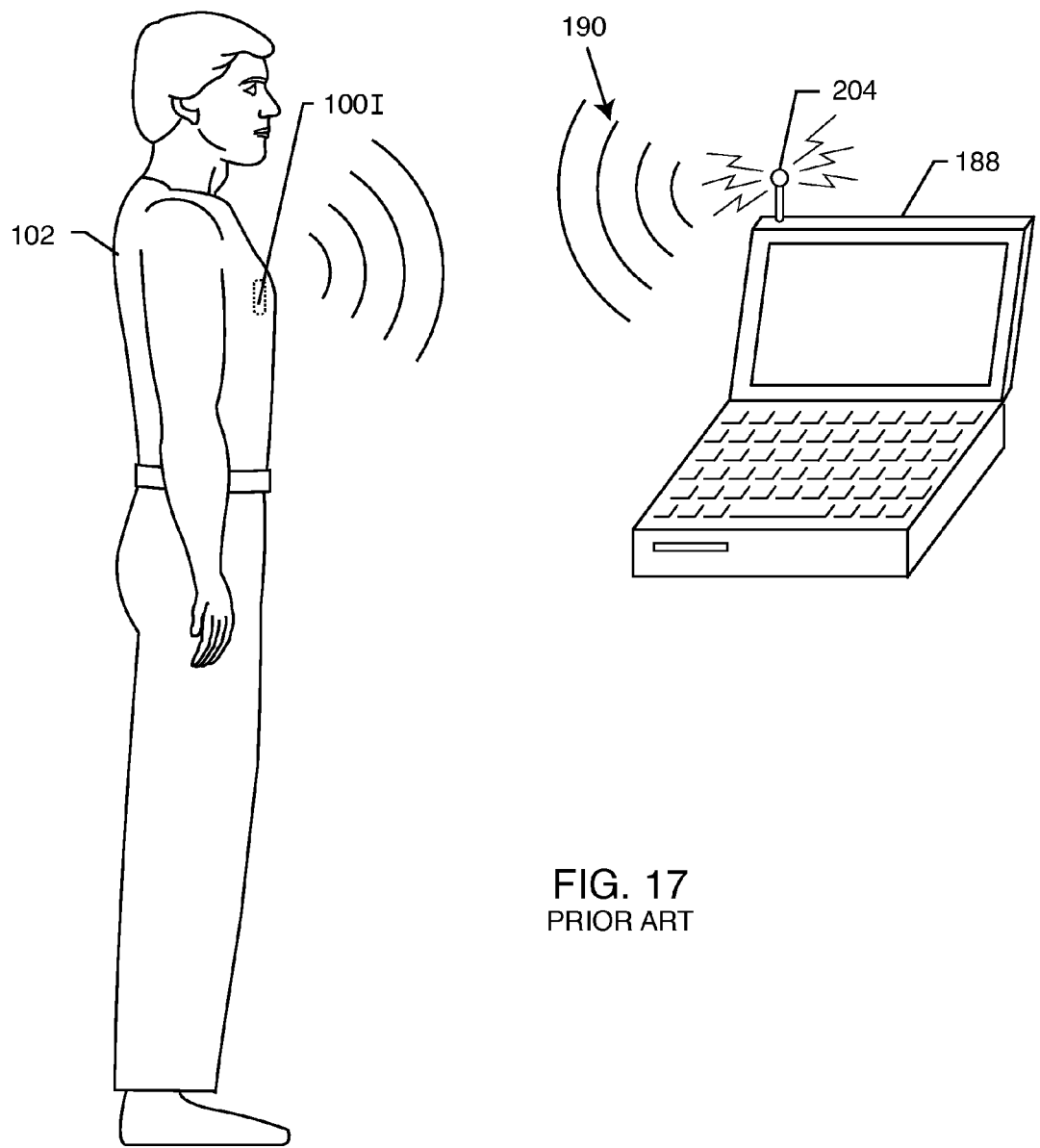
FIG. 17 is a depiction of a patient fitted with an ICD communicating with an external programmer.

FIG. 15 illustrates an electrical schematic embodying the present invention and is an electrical block diagram of the ICD's high voltage charging circuitry. First of all, as previously described, there is a communication interface 186 from an external programmer 188 to internal circuits 130 within the ICD100I. The external programmer 188 can be close coupled wanded telemetry (FIG. 18) or RF distance telemetry (FIG. 17). The communication interface electronics 186 and processor 130 of the ICD100I can be contained on one or more circuit boards 130 previously illustrated in FIG. 5. All of these circuits are typically contained inside the hermetically sealed housing 124 of the ICD100I. The communication circuit 186 interfaces with a processor 130 which has unique program functions. When the ICD100I is switched from a first mode and into a second (MRI) mode, by means of a signal 190 from the external programmer 188 to the communication interface 186, the processor 130 directs the DC to AC converter 180, which is typically a switch mode power supply 180, to convert low voltage DC energy from the battery 178 to a low voltage AC. This low voltage AC is directed to the primary winding 194 of a transformer 172. The secondary winding 194, which has a much higher number of turns than the primary winding 192, transforms the low voltage AC to a high voltage AC. This AC voltage is then rectified in the AC to DC rectifier 182 and the output is used to charge the ICD's energy storage capacitor 176.

It should be noted that the high voltage storage capacitor 176 can actually consist of a number of capacitors acting either in series or parallel. For the purposes herein, it will be described as a capacitor (singular).

At this point, the energy storage capacitor 176 is fully charged and is ready to deliver high voltage therapy. The capacitor 176 will remain in this charged state until it either delivers therapeutic energy to the patient 102 or a specific instruction may be made for a bleeder resistor 196 to be switched in through bleeder switch 198 which would then bleed off the high voltage energy and thereby discharge capacitor 176. In the MRI-ready mode, the capacitor 176 is fully charged and its high voltage electronic switch(es) 184 are ready to deliver the energy in the high voltage storage capacitor 176 to implanted electrodes 164, 166.

It should be noted that there is a programmable switch 200 which can use the housing 124 of the ICD100I as an electrode or can be switched (as shown) to a second electrode within or adjacent the human heart. Accordingly, if the ICD senses a dangerous ventricular arrhythmia, the processor 130 instructs switch 184 to close and thereby deliver a high voltage lifesaving shock to the patient 102. Upon completion of the MRI scanning, the ICD100I is returned to its first or normal operating mode, while at the same time, the bleeder 196 may be switched 198 in such that it will bleed off the charge on the high voltage capacitor 176. The ICD100I may be returned to its original mode from a timer 202 located within the processor that runs for a pre-set amount of time, by the static magnetic field sensor, or by a second signal 190 being sent from the external programmer 188.

Figure 16:
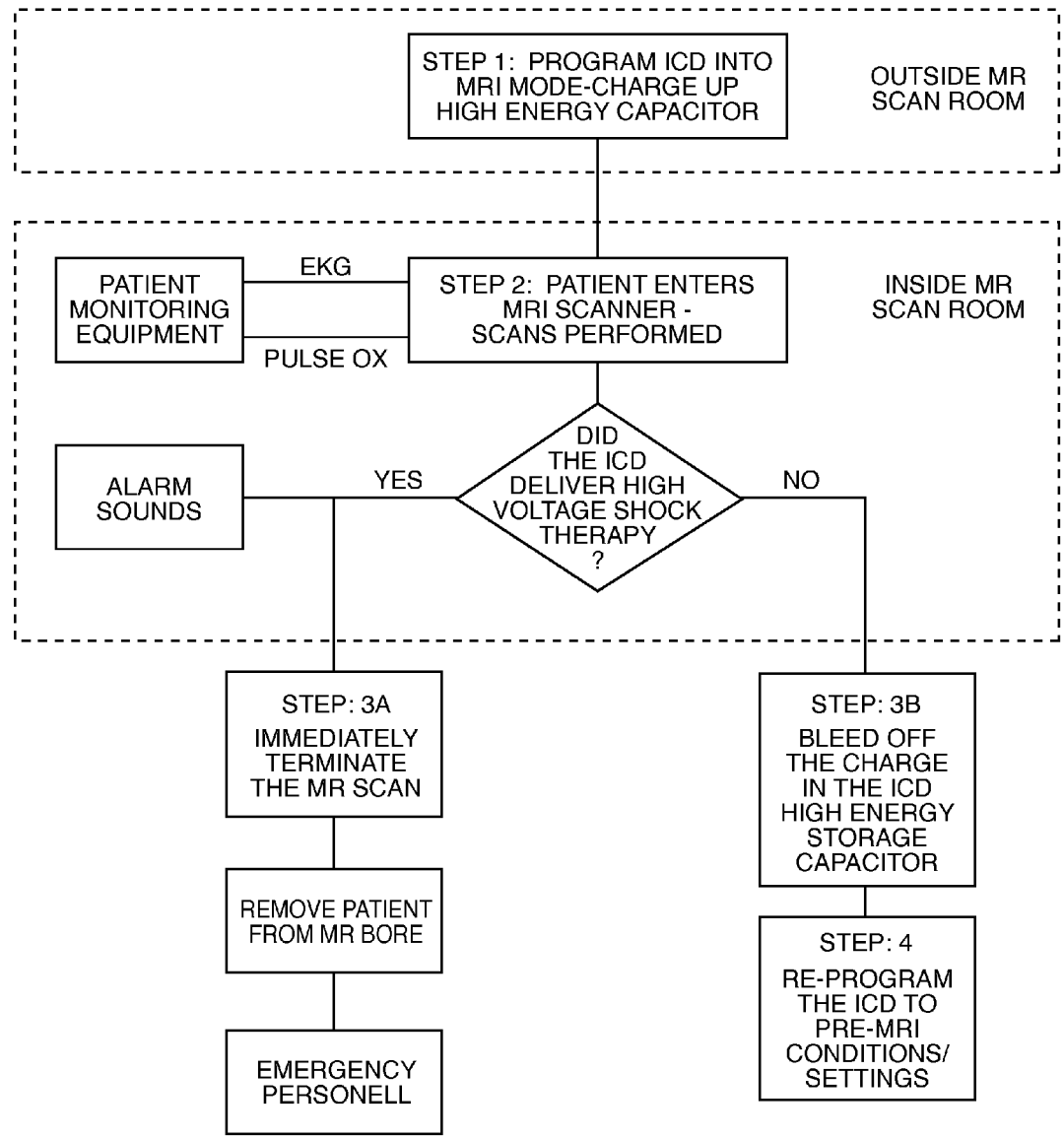
FIG. 16 illustrates a block diagram showing the steps of an embodiment of the present invention.

FIG. 16 illustrates a block diagram showing the steps of an embodiment of the present invention. In step 1, the patient 102 is outside the MRI scan room (or at least 10 feet from the MRI scanner bore). In step 1, the ICD100I is programmed into its MRI mode. This can include a number of things, but in particular, in accordance with the present invention, the energy storage capacitor 176 is fully charged up. In a preferred embodiment, the energy storage capacitor 176 is charged up to its full capacity. In addition, the ICD100I has been especially designed (or software programmed) such that the ICD energy storage capacitor 176 will maintain this charge throughout the length of a typical MRI scan (~20 to 60 minutes).

In step 2, the patient 102 has entered the scan room and has been conveyored into the MRI bore 104. In a preferred embodiment, EKG electrodes and pulse ox monitors have been placed on the patient 102 so that the patient 102 may be continuously monitored during the MRI scans. In particular, an external monitor is connected to the patient. This special external monitor also monitors for a high voltage shock delivery. In the case where the ICD100I does deliver high voltage shock therapy, this monitor immediately triggers an alarm alerting the MRI scan technician and/or radiologist that the patient has undergone a defibrillation shock. Other preferred monitors include constant EKG monitoring and pulse ox. The pulse ox monitors blood oxygen levels. If a patient's pulse oxygen level decrease, this is an immediate warning of a dangerous ventricular arrhythmia.

Step 3A occurs if the ICD100I did indeed deliver high voltage shock therapy. In this case, in step 3A, the external monitors deliver an alarm and the scan is immediately terminated. The patient in step 3*b* is quickly removed from the MRI bore and taken at least several feet from it (10 feet would be the preferred minimum). Then emergency personnel are summoned. The reason the patient is removed quickly from the bore and taken some distance from the bore is so the ICD and internal electronics and in particular the high voltage charging circuit can again operate properly. In this case, the energy storage capacitor of the ICD could be recharged so that one or more additional clinical shocks could be delivered to the patient if necessary.

In the case in step 3*b*, where the ICD did not deliver a shock therapy during the MR scan, the patient is then removed from the bore 104 (at a more leisurely pace) and then the charge may be bled off the energy storage capacitor 176. In step 4 the ICD is reprogrammed to its pre-MRI conditions and settings.

In another exemplary embodiment of the present invention, there is a distinction between stored charge energy and shock delivery energy. In step 1 the high energy storage capacitor 176 is fully charged up. Over the length of time during an MRI procedure, the high energy storage capacitor 176 may lose some of its initial energy. This means that the joules delivered and the voltage delivered will be lower than when it was fully charged before starting the MRI procedure. In exemplary embodiments, the stored energy charge should be a minimum of 10 joules such that at a later time the shock delivery energy would be approximately 5 joules or more. This means that after a period of time, for example 20-40 minutes, the high energy storage capacitor 176 can still deliver a clinically significant energy level shock even though there has been degradation and bleed-off of the stored energy. In other exemplary embodiments, the initial stored energy charge could be upwards of 45 joules. Also, the initial stored charge voltage could be 700-900 volts or more. Therefore, during the MRI procedure the shock delivery voltage may be around 600-800 volts. If the voltage is too low, it may not convert the heart 112 effectively. Other degradation and bleed-off rates may be accounted for by the present invention by those skilled in the art as this disclosure is not limited to the specific embodiments disclosed herein.

Now discussing time-related voltage decay in more detail, it has been seen through the applicant's research and development that a typical voltage decay of a wet tantalum capacitor stack is approximately 35 percent in 60 minutes. This means that a capacitor stack charged to 765 volts may decay to approximately 500 volts in an hour. Therefore, it would be safe to generalize that in a typical device the voltage would drop by less than 35 percent in 40 minutes. Furthermore, it would be safe to generalize that the energy stored in a capacitor after an hour would decay by less than 50 percent. If the capacitor stack was charged initially and stored 44 joules of energy (at 765 volts), in 60 minutes the stored energy would decay to a value greater than 22 joules. Therefore, it may be generalized that the stored energy after 30-40 minutes would be at least 50 percent of the initial energy. In other words, 44 joules would decay to a value greater than 22 joules after 30-40 minutes.

Understanding that the shock delivery energy will be lower than the initial stored charge energy due to time-related decay, the delivered energy to the patient for therapy will also be lessened due to losses in the discharge process and truncation of the discharge curve. These losses are a function of the cycle efficiency of the capacitor. If after 30-40 minutes, the capacitor has more than 22 joules of energy stored, the amount of energy actually delivered to the heart 112 for therapy will be roughly above 70 percent of the 22 joules, or greater than 15 joules of energy. Therefore, for a typically implantable cardioverter defibrillator 100I with 44 joules of stored energy in the capacitor, after 30-40 minutes the amount of energy actually delivered for therapy will be about 20 to 30 joules of energy. The present invention accounts for these various losses and other losses not specifically described herein, and is not limited in application to just the specific losses described.

FIG. 17 illustrates an ICD patient 102 with an implantable cardioverter defibrillator (ICD) shown as 100I. A prior art external programmer 188 is shown along with an RF distance telemetry antenna 204. RF distance telemetry has become quite popular in recent years as opposed to the old style wanded telemetry. The external programmer 188 can send and receive electromagnetic signals 190 to and from the implanted ICD100I. In this case, the ICD100I has its own RF telemetry transceiver and antenna (not shown). In the present invention, the ICD external programmer 188 would have software modifications and perhaps hardware modifications so that it could transmit a signal 190 which causes the ICD100I to switch between a first mode and a second mode.

The first mode would be its normal operating mode. The second mode would put it into its MRI mode, where in accordance with the present invention, the storage capacitor 176 would be charged up such that it is ready to deliver an appropriate therapeutic shock while inside of an MRI bore 104.

Figure 18:
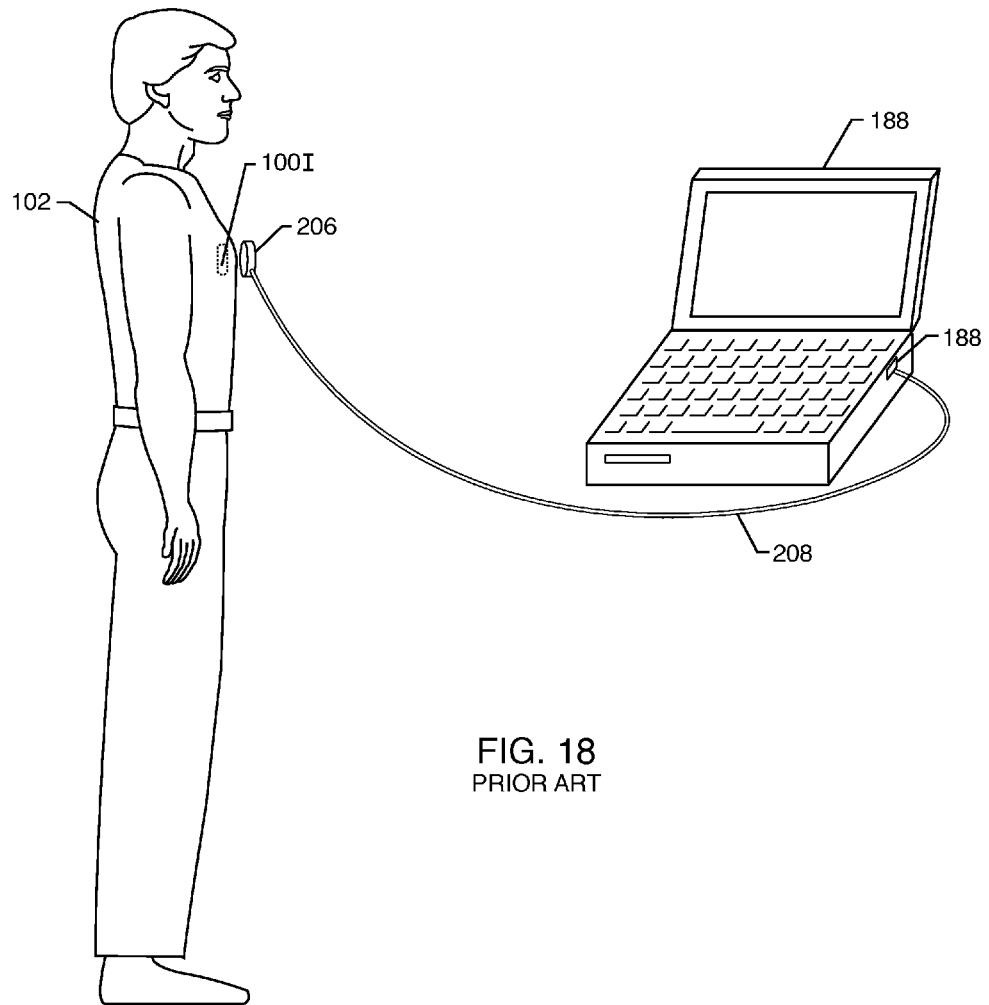
FIG. 18 is a depiction of a patient fitted with an ICD communicating with a wand connected to an external programmer.

FIG. 18 is very similar to FIG. 17 except this illustrates the old style wanded telemetry 206. In this case, the wand or telemetry head 206 is placed directly over the ICD100I. A cable 208 connects the telemetry wand 206 directly to the external programmer 188. This system is effective, but is less convenient as it often takes a bit of time to get the wand 206 exactly in the right position so that it will communicate with the ICD100I. Wanded telemetry depends upon closely coupled inductive coils, one of which is placed in the wand 206 and the other inside or adjacent to the ICD itself. Coupling range is usually limited to a few centimeters at best. As previously discussed in FIG. 17, close-wanded telemetry can be used to switch the ICD100I between a first and a second mode.

Figure 19:
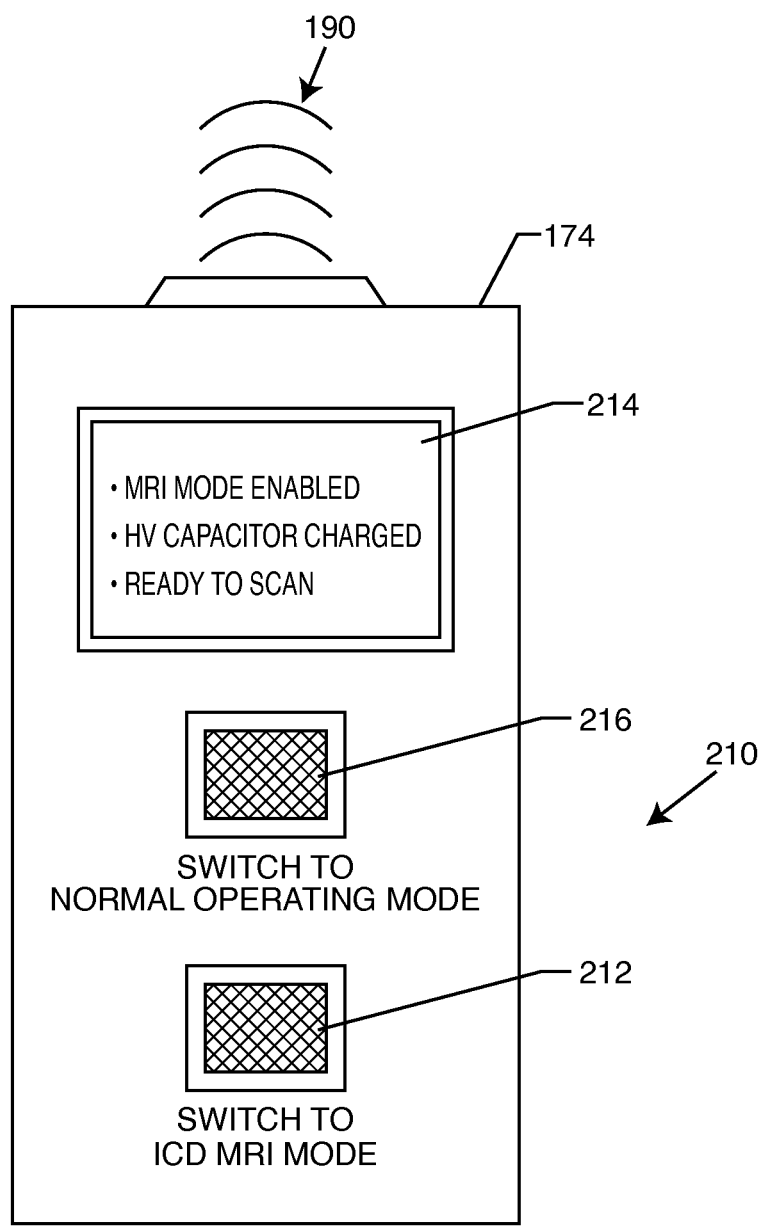
FIG. 19 is an illustration of a novel external programmer embodying the present invention.

FIG. 19 illustrates a novel hand-held external programmer 210 of the present invention. This unit 210 is battery operated and self-contained and can also send a signal 190 to the implanted medical device 100I causing it to switch between the first and second modes as previously described. This unit 210 is relatively inexpensive and very portable such that every MRI suite could have one. As previously described for FIGS. 17 and 18, the hand-held novel programmer 210 can send and receive signals from the implanted ICD100I. For example, while outside the MRI chamber 104, a button 212 on the hand-held external programmer 210 is pushed thereby sending a signal 190 to the ICD100I. At that point, a digital display 214 would indicate that the MRI mode has been enabled. Then a blinking light or other indicator would come on until the energy storage capacitor 176 is fully charged up. At that time, an indication would come on indicating that the patient's ICD100I is ready to be scanned and/or that the energy storage capacitor 176 is fully charged. In accordance with the present invention, the patient 102 would stay in the second mode for a predetermined amount of time, which would require a timing circuit 202, or in an alternative embodiment, the ICD 100I would stay in its second mode indefinitely until the patient 102 was removed from the MRI chamber and a second button 216 (or buttons) would be pushed on the hand-held external programmer 210, which would cause the energy capacitor 176 to have its energy bled off and the ICD100I returned to its first mode, which is its normal operating mode. It will be obvious to those skilled in the art that the two buttons, as shown in FIG. 19, as 212 and 216 could be combined into a single toggle-type button, which could also switch modes.

Figure 20:
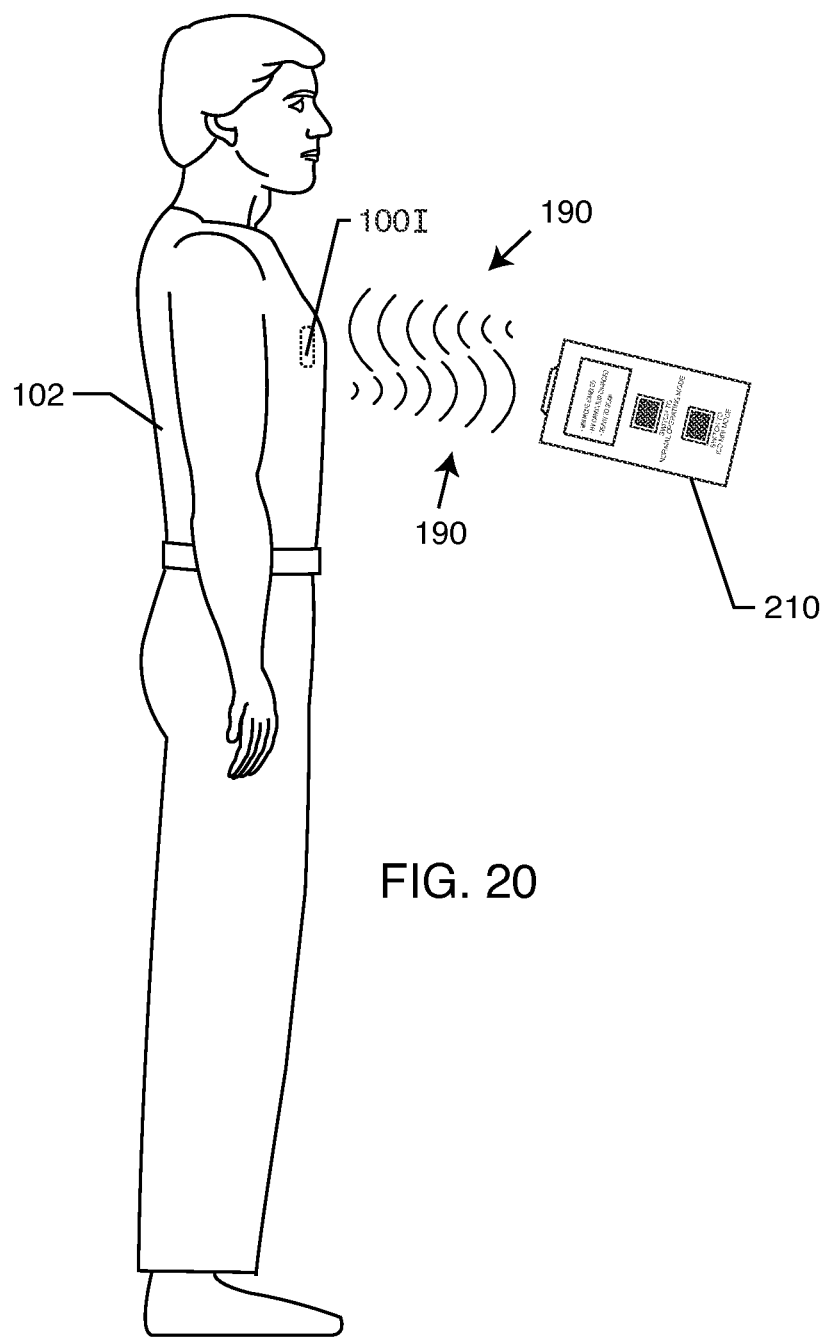
FIG. 20 is a depiction of a patient fitted with an ICD communicating with the novel external programmer shown in FIG. 19.

FIG. 20 illustrates the novel programmer 210 of FIG. 19 being directed at a patient 102 transmitting electromagnetic signals 190. The communication shown in FIG. 20 can be used either to place an ICD100I into a second MRI mode, or upon completion of the MRI, it could be used to return the ICD100I to its first or normal operating mode.

Although several embodiments have been described in detail for purposes of illustration, various modifications may be made to each without departing from the scope and spirit of the invention. Accordingly, the invention is not to be limited, except as by the appended claims.

What is claimed is:

1. A method of performing a magnetic resonance imaging (MRI) scan on a patient having an implanted cardioverter defibrillator (ICD), comprising the steps of:
   determining that the ICD comprises a ferrite core high voltage power supply transformer;

with the ICD not being in the presence of an MRI field generated by an MRI scanner, sending a communication signal from an external programmer to the ICD, the communication signal being a command to precharge an energy storage capacitor of the ICD before the patient undergoes an MRI scan, the command also switching the ICD into an MRI mode, where the MRI mode is configured to autonomously detect a dangerous ventricular arrhythmia and when needed deliver a precharged defibrillation shock;

moving the patient into the MRI scanner;

performing the MRI scan;

removing the patient from the MRI scanner after the MRI scan is completed or after the ICD delivers a first defibrillation shock to the patient while in the presence of the MRI field;

moving the patient substantially away from the MRI field; and determining that the ICD has not delivered the first defibrillation shock and allowing the ICD to automatically bleed off a first electrical charge stored in the energy storage capacitor, or if the ICD has delivered the first defibrillation shock and it is determined that additional therapy is needed, allowing the ICD to recharge the energy storage capacitor and deliver a second defibrillation shock to the patient.

2. The method of claim 1, including the step of monitoring the status of the patient or ICD while performing the MRI scan.

3. The method of claim 2, wherein monitoring the status of the patient comprises monitoring EKG or pulse ox of the patient.

4. The method of claim 3, including the step of sounding an alarm for emergency personnel when the ICD delivers the first defibrillation shock.

5. The method of claim 1, wherein the step of performing the MRI scan comprises more than 20 minutes.

6. The method of claim 1, wherein the first or second defibrillation shocks each comprise at least 15 joules.

7. The method of claim 1, wherein the first or second defibrillation shocks each comprise at least 30 joules.

8. The method of claim 1, including the step of sending a second communication signal from the external programmer to the ICD, wherein the second communication signal comprises a second command to switch the ICD to a non-MRI mode.

9. The method of claim 1, wherein the ICD comprises a magnetic field sensor in electrical communication with a processor for the ICD and wherein the processor is configured to switch the ICD to a non-MRI mode when the magnetic field sensor detects a lack of a static magnetic field, and including the step of allowing the ICD to switch to the non-MRI mode.

10. A method of performing a magnetic resonance imaging (MRI) scan on a patient having an implanted cardioverter defibrillator (ICD), comprising the steps of:

providing the ICD comprising:
a hermetically sealed housing;
a communication interface disposed within the housing operable to receive a communication signal from an external programmer, wherein the communication signal comprises a command to switch the ICD in the absence of a dangerous ventricular arrhythmia from a normal operating mode to an MRI mode;
a processor disposed within the housing in electrical communication with the communication interface, the processor configured to switch the ICD between the normal operating and MRI modes;
a battery disposed within the housing configured to supply a low DC voltage;
a converter comprising a ferrite core transformer disposed within the housing configured to convert the low DC voltage to a high DC voltage; and
an energy storage capacitor disposed within the housing electrically coupled to the converter, wherein the energy storage capacitor is configured to store the high DC voltage;
wherein the MRI mode comprises precharging the energy storage capacitor by activating the converter to convert the low DC voltage to the high DC voltage and storing the high DC voltage within the energy storage capacitor during a period of time of the MRI mode, wherein the MRI mode is configured to autonomously detect the dangerous ventricular arrhythmia, where the implantable cardioverter defibrillator is precharged outside the presence of an MRI main static field and then can deliver a first defibrillation shock while in the presence of the MRI main static field;

with the ICD not being in the presence of the MRI main static field generated by an MRI scanner, sending the communication signal from the external programmer to the ICD, the communication signal being the command to switch the ICD from the normal operating mode to the MRI mode thereby charging the energy storage capacitor of the ICD before the patient undergoes an MRI scan;

moving the patient into the MRI scanner;

performing the MRI scan;

removing the patient from the MRI scanner after the MRI scan is completed or after the ICD delivers the first defibrillation shock while in the presence of the MRI main static field;

moving the patient substantially away from the MRI main static field; and determining that the ICD has not delivered the first defibrillation shock and allowing the ICD to automatically bleed off a first electrical charge stored in the energy storage capacitor, or if the ICD has delivered the first defibrillation shock and it is determined that additional therapy is needed, allowing the ICD to recharge the energy storage capacitor and deliver a second defibrillation shock to the patient.

11. The method of claim 10, including the step of monitoring the status of the patient or ICD while performing the MRI scan.

12. The method of claim 11, wherein monitoring the status of the patient comprises monitoring EKG or pulse ox of the patient.

13. The method of claim 12, including the step of sounding an alarm for emergency personnel when the ICD delivers the first defibrillation shock.

14. The method of claim 10, wherein the step of performing the MRI scan comprises more than 20 minutes.

15. The method of claim 10, wherein the first or second defibrillation shock comprises at least 15 joules.

16. The method of claim 10, wherein the first or second defibrillation shock comprises at least 30 joules.

17. The method of claim 10, including the step of sending a second communication signal from the external programmer to the ICD, wherein the second communication signal comprises a second command to switch the ICD from the MRI mode to the normal operating mode.

18. The method of claim 10, wherein the ICD comprises a magnetic field sensor in electrical communication with the processor and wherein the processor is configured to switch the ICD from the MRI mode to the normal operating mode when the magnetic field sensor detects a lack of a static magnetic field, and including the step of allowing the ICD to switch from the MRI mode to the normal operating mode.

19. A method of performing a magnetic resonance imaging (MRI) scan on a patient having an implanted cardioverter defibrillator (ICD), comprising the steps of:
- determining that the ICD comprises a ferrite core transformer that is a component of a high energy storage capacitor charging circuit;
- with the ICD not being in the presence of an MRI main static field generated by an MRI scanner, sending a communication signal from an external programmer to the ICD, the communication signal being a command to charge the high energy storage capacitor of the ICD before the patient undergoes an MRI scan, the command also switching the ICD into an MRI mode, where the MRI mode is configured to autonomously detect a dangerous ventricular arrhythmia and when needed deliver a precharged defibrillation shock;
- moving the patient in close proximity to the MRI scanner;
- performing the MRI scan comprising more than 20 minutes;
- removing the patient from close proximity to the MRI scanner when the MRI scan is completed or when the ICD delivers a first defibrillation shock of at least 15 joules while in the presence of the MRI field;
- moving the patient substantially away from the MRI field; and
- determining that the ICD has not delivered the first defibrillation shock and allowing the ICD to automatically bleed off a first electrical charge stored in the high energy storage capacitor, or if the ICD has delivered the first defibrillation shock and it is determined that additional therapy is needed, allowing the ICD to recharge the high energy storage capacitor and deliver a second defibrillation shock to the patient.

20. The method of claim 19, including the step of sending a second communication signal from the external programmer to the ICD, wherein the second communication signal comprises a second command to switch the ICD to a non-MRI mode.

21. The method of claim 19, wherein the ICD comprises a magnetic field sensor in electrical communication with the processor and wherein the processor is configured to switch the ICD to a non-MRI mode when the magnetic field sensor detects a lack of a static magnetic field, and including the step of allowing the ICD to switch to the non-MRI mode.

* * * * *

UNITED STATES PATENT AND TRADEMARK OFFICE
CERTIFICATE OF CORRECTION

PATENT NO.        : 9,101,782 B2                                    Page 1 of 1
APPLICATION NO.   : 13/958582
DATED             : August 11, 2015
INVENTOR(S)       : Dominick J. Frustaci, Barry C. Muffoletto and Robert A. Stevenson It is certified that error appears in the above-identified patent and that said Letters Patent is hereby corrected as shown below:

On the title page, item 56

Page 2, 30th reference in U.S. PATENT DOCUMENTS delete "Stvenson" and insert --Stevenson--

In the drawings

Sheet 10 of 15, Figure 15 item 188 delete "PROGRAMER" and insert --PROGRAMMER--

Signed and Sealed this
Fifth Day of January, 2016

Michelle K. Lee
*Director of the United States Patent and Trademark Office*